(12) United States Patent
Kawagishi et al.

(10) Patent No.: US 9,738,063 B2
(45) Date of Patent: Aug. 22, 2017

(54) METHOD AND APPARATUS FOR MANUFACTURING WELDED RESIN ARTICLE

(71) Applicant: NGK SPARK PLUG CO., LTD., Nagoya-shi, Aichi (JP)

(72) Inventors: Wataru Kawagishi, Ichinomiya (JP); Shinji Kumazawa, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 176 days.

(21) Appl. No.: 14/483,573

(22) Filed: Sep. 11, 2014

(65) Prior Publication Data

US 2015/0075700 A1 Mar. 19, 2015

(30) Foreign Application Priority Data

Sep. 12, 2013 (JP) .................................. 2013-189300
Apr. 23, 2014 (JP) .................................. 2014-088648

(51) Int. Cl.
*B32B 41/00* (2006.01)
*B29C 65/82* (2006.01)
(Continued)

(52) U.S. Cl.
CPC .......... *B32B 41/00* (2013.01); *B29C 65/1635* (2013.01); *B29C 65/1654* (2013.01);
(Continued)

(58) Field of Classification Search
CPC ............ B29C 65/1635; B29C 65/1654; B29C 65/1658; B29C 65/1661; B29C 66/43;
(Continued)

(56) References Cited

U.S. PATENT DOCUMENTS 7,651,264 B2 1/2010 Matsumoto et al.
7,910,153 B2 3/2011 Kawagoe et al.
(Continued)

FOREIGN PATENT DOCUMENTS

JP 3939205 B2 7/2007
JP 4577103 B2 11/2010

OTHER PUBLICATIONS

Paul Horowitz and Winifield Hill, The Art of Electronics, 2nd Edition, Cambridge University Press, 1995, pp. 1026-1031.*

*Primary Examiner* — George Koch
(74) *Attorney, Agent, or Firm* — Sughrue Mion, PLLC

(57) ABSTRACT

A method and apparatus for manufacturing a welded resin article which includes (a) bringing first and second resin members to come into contact with each other; (b) applying laser light to the first and second resin members while moving the laser light relative to the first and second resin members; (c1) obtaining a value corresponding to the intensity of infrared light from a plurality of locations on a surface; (d) successively calculating, as a section average, the average of a predetermined number of successive values, among those obtained from the plurality of locations corresponding to the intensity of the infrared light; (e) a step of successively calculating a deviation judgment value; and (f) a step of successively judging whether or not the deviation judgment value falls within a predetermined judgment threshold range.

16 Claims, 17 Drawing Sheets

(51) Int. Cl.
| | |
|---|---|
| *B29C 65/16* | (2006.01) |
| *B29C 65/00* | (2006.01) |
| *G01N 25/72* | (2006.01) |
| *G01N 33/44* | (2006.01) |
| *B29L 9/00* | (2006.01) |

(52) U.S. Cl.
CPC ...... *B29C 65/8253* (2013.01); *B29C 66/1122* (2013.01); *B29C 66/24244* (2013.01); *B29C 66/43* (2013.01); *B29C 66/5346* (2013.01); *B29C 66/7373* (2013.01); *B29C 66/91216* (2013.01); *B29C 66/91221* (2013.01); *B29C 66/9592* (2013.01); *G01N 25/72* (2013.01); *G01N 33/442* (2013.01); *B29C 65/1677* (2013.01); *B29C 66/71* (2013.01); *B29C 66/721* (2013.01); *B29C 66/7212* (2013.01); *B29C 66/73921* (2013.01); *B29C 66/863* (2013.01); *B29C 66/939* (2013.01); *B29L 2009/00* (2013.01)

(58) Field of Classification Search
CPC ........ B29C 66/91216; B29C 66/91221; B29C 66/939; B29C 66/9592; B32B 41/00; G01N 25/72; G01N 33/442
USPC .......................................................... 156/64
See application file for complete search history.

(56) References Cited

U.S. PATENT DOCUMENTS

| | | | |
|---|---|---|---|
| 8,727,610 | B2 | 5/2014 | Matsumoto et al. |
| 2005/0169346 | A1* | 8/2005 | Murray ............... B23K 26/032 374/121 |
| 2006/0153270 | A1 | 7/2006 | Matsumoto et al. |
| 2006/0278113 | A1* | 12/2006 | Kawagoe ............ B29C 65/1635 101/494 |
| 2007/0084552 | A1* | 4/2007 | Watanabe ........... B29C 65/1635 156/272.8 |
| 2010/0140233 | A1 | 6/2010 | Matsumoto et al. |

* cited by examiner

METHOD AND APPARATUS FOR
MANUFACTURING WELDED RESIN
ARTICLE

BACKGROUND OF THE ART

1. Field of the Invention

The present invention relates to a method and apparatus for manufacturing a welded resin article.

2. Description of the Related Art

Conventionally, a technique has been known of judging the state of welding between resin members joined by laser welding (hereinafter, referred to as the "weld state"). Examples of the technique of judging whether the weld state is good or bad are disclosed in the Patent Documents listed below.

PATENT DOCUMENTS

[Patent Document 1] Japanese Patent Application Laid-Open (kokai) No. 2004-17120
[Patent Document 2] Japanese Patent Application Laid-Open (kokai) No. 2006-341563

3. Problems to be Solved by the Invention

However, the techniques described in the above-listed Patent Documents lack sufficient studies and methodology for judging the weld state in the case where a foreign substance is present on the surface of a resin member or between resin members.

SUMMARY OF THE INVENTION

The present invention has been made in order to address the above-mentioned problems, and an object thereof is to provide a method and apparatus which enables manufacture of a welded resin article having a good weld state.

The above object has been achieve, in a first aspect of the invention, by providing (1) a method of manufacturing a welded resin article by laser-welding together a first resin member which allows laser light to pass therethrough and a second resin member which absorbs the laser light. The method comprises (a) a step of bringing the first resin member and the second resin member into contact with each other or close to (in the vicinity of) each other; (b) a step of applying the laser light to a surface of the second resin member from a side where the first resin member is present, while moving the laser light relative to the first and second resin members; (c1) a step of obtaining a value corresponding to the intensity of infrared light emitted from the surface that is heated as a result of applying the laser light, the value being obtained from individual ones of a plurality of locations on the surface as a result of relative movement of the laser light; (d) a step of successively calculating a section average which is the average of a predetermined number of successive values, the number being equal to or greater than 2, among the values obtained from the plurality of locations on the surface and each corresponding to the intensity of the infrared light; (e) a step of successively calculating a deviation judgment value representing the degree of deviation of the value corresponding to the intensity of the infrared light from the section average; and (f) a step of successively judging whether or not the deviation judgment value falls within a predetermined judgment threshold range and judging that a weld state at the surface is good when the deviation judgment value falls within the judgment threshold range.

In the case where a foreign substance is present on the surface of the first resin member or between the first resin member and the second resin member, the value corresponding to the intensity of infrared light emitted from the surface of the second resin member deviates from the section average. According to the present mode, the presence/absence of a foreign substance can be detected. Therefore, it is possible to judge that the weld state is good when no foreign substance is present and to manufacture a welded resin article having a good weld state.

In a second aspect, the present invention provides (2) a method of manufacturing a welded resin article by laser-welding together a first resin member which allows laser light to pass therethrough and a second resin member which absorbs the laser light. The method comprises (a) a step of bringing the first resin member and the second resin member into contact with each other or close to each other; (b) a step of applying the laser light to a surface of the second resin member from a side where the first resin member is present, while moving the laser light relative to the first and second resin members; (c1) a step of obtaining a value corresponding to the intensity of infrared light emitted from the surface that is heated as a result of applying the laser light, the value being obtained from individual ones of a plurality of locations on the surface as a result of relative movement of the laser light; (c2) a step of calculating a value relating to the temperature of the surface irradiated with the laser light based on the value corresponding to the intensity of the infrared light; (c3) a step of judging whether or not the value relating to the temperature falls outside a predetermined temperature threshold range and judging that a weld state at the surface is good when the value relating to the temperature does not fall outside the predetermined temperature threshold range; (d) a step of calculating, when the weld state at the surface is not judged in the step (c3) to be good, a section average which is the average of a predetermined number of successive values, the number being equal to or greater than 2, among the values obtained from the plurality of locations on the surface and each corresponding to the intensity of the infrared light; (e) a step of calculating a deviation judgment value representing the degree of deviation of the value corresponding to the intensity of the infrared light from the section average; and (f) a step of judging whether or not the deviation judgment value falls within a predetermined judgment threshold range and judging that the weld state at the surface is good when the deviation judgment value falls within the predetermined judgment threshold range.

In the case where a foreign substance is present on the surface of the first resin member or between the first resin member and the second resin member, the value relating to the temperature of the surface irradiated with the laser light deviates from a predetermined temperature threshold range. According to the present mode, the presence/absence of a foreign substance can be detected. Therefore, it is possible to judge that the weld state is good when no foreign substance is present and to manufacture a welded resin article whose weld state is good.

In a preferred embodiment (3) of the method of manufacturing a welded resin article according to (1) or (2) above, the step (c1) includes a step of obtaining values corresponding to the intensities of two infrared lights having different wavelengths, and the method includes a step of calculating a ratio between the values corresponding to the intensities of the two infrared lights and using the ratio as the value corresponding to the intensity of the infrared light.

According to this mode, when the value relating to the temperature is calculated, a two-color method can be used.

In another preferred embodiment (4) of the method of manufacturing a welded resin article according to (1) or (2) above, the step (c1) includes a step of obtaining values corresponding to the intensities of two or more infrared lights having different wavelengths, and the steps subsequent to the step (c1) may be performed for each of the values corresponding to the intensities of the two or more infrared lights having different wavelengths.

According to this mode, the weld state is judged based on the values corresponding to the intensities of two or more infrared lights. Therefore, the accuracy in judging the weld state can be increased.

In yet another preferred embodiment (5) of the method of manufacturing a welded resin article according to any of (1) to (4) above, the section average in the step (d) is a moving average in a section in which the value corresponding to the intensity of the infrared light is contained, the moving average being calculated from the value corresponding to the intensity of the infrared light, one or more such values preceding the value corresponding to the intensity of the infrared light, and one or more such values following the value corresponding to the intensity of the infrared light.

According to this mode, it is possible to calculate a proper section average for calculation of the deviation judgment value.

In yet another preferred embodiment (6) of the method of manufacturing a welded resin article according to any of (1) to (5) above, the step (e) comprises a step of calculating the deviation judgment value by subtracting the section average from the value corresponding to the intensity of the infrared light.

According to this mode, it is possible to properly calculate the degree of deviation of the value corresponding to the intensity of infrared light from the section average.

In yet another preferred embodiment (7) of the method of manufacturing a welded resin article according to any of (1) to (6) above, the step (f) includes a step of defining as a peculiar deviation judgment value a deviation judgment value which does not fall within the predetermined judgment threshold range and calculating an added deviation judgment value by adding together the peculiar deviation judgment value, one or more deviation judgment values preceding the peculiar deviation judgment value and one or more deviation judgment values following the peculiar deviation judgment value; and a step of judging whether the weld state at the surface is good or bad by comparing the added deviation judgment value with a predetermined deviation judgment threshold.

In the case where a foreign substance is present on the surface of the first resin member or between the first and second resin members and the foreign substance is a combustible foreign substance which burns and vaporizes when irradiated with the laser light, at the time of burning of the foreign substance, instantaneous ignition occurs and strong light is emitted. Therefore, the added deviation judgment value becomes greater than the predetermined deviation judgment threshold. In contrast, in the case where the foreign substance is an incombustible foreign substance which does not vaporize even when irradiated with the laser light and which blocks the laser light, the added deviation judgment value becomes smaller than the predetermined deviation judgment threshold. Since a combustible foreign substance vaporizes when irradiated with laser light, the weld state at the surface is good. Since an incombustible foreign substance blocks laser light, an unwelded portion may be produced on the surface. According to this mode, the judgment as to whether the foreign substance is a combustible foreign substance or an incombustible foreign substance is made on the basis of the added deviation judgment value. Therefore, the judgment as to whether the weld state is good (acceptable) or bad (unacceptable) can be performed properly.

In yet another preferred embodiment (8) of the method of manufacturing a welded resin article according to (7) above, the step (f) includes a step which is performed when a plurality of deviation judgment values falling outside the predetermined judgment threshold range are present successively and which comprises defining, as the peculiar deviation judgment value, one of the plurality of successive deviation judgment values which is most remote from the predetermined judgment threshold range.

In the case where a foreign substance is present on the surface of the first resin member or between the first and second resin members, the deviation judgment value at a position where burning of the foreign substance or blocking of the laser light by the foreign substance becomes most noticeable is most remote from the predetermined judgment threshold range. According to this mode, the deviation judgment value at a position where burning of the foreign substance or blocking of the laser light by the foreign substance becomes most noticeable is defined as a peculiar deviation judgment value, and the combustibility of the foreign substance is judged. Therefore, the judgment as to whether the weld state is good or bad can be performed properly.

In yet another preferred embodiment (9) of the method of manufacturing a welded resin article according any of (1) to (8) above, the step (f) includes a step of judging that the weld state at the surface is bad when a predetermined number of deviation judgment values falling outside the predetermined judgment threshold range are present successively.

In the case where a foreign substance is present on the surface of the first resin member or between the first and second resin members and the size of the foreign substance is equal to or greater than a predetermined size, the number of successive deviation judgment values falling outside the predetermined judgment threshold range becomes equal to or greater than a predetermined number. In the case where the size of the foreign substance is equal to or greater than the predetermined size, the possibility that the weld state is bad is high even when the foreign substance is a combustible foreign substance. According to this mode, the judgment as to whether the size of the foreign substance is equal to or greater than a predetermined size is made. Therefore, the judgment as to whether the weld state is good or bad can be performed properly.

In yet another preferred embodiment (10) of the method of manufacturing a welded resin article according to any of (1) to (9) above, the welded resin article is a resin housing.

According to this mode, a resin housing whose weld state is good can be manufactured.

The present invention can be embodied in various forms other than the method of manufacturing a welded resin article. For example, the present invention be realized in the form of an apparatus for manufacturing a welded resin article, in the form of a weld state judgment apparatus, in the form of a weld state judgment method, in the form of a computer program for realizing the weld state judgment method, or in the form of a non-temporary storage medium which stores the computer program.

Thus, in a third aspect (11), the present invention provides an apparatus for manufacturing a welded resin article, comprising: a laser irradiation apparatus which applies laser light to first and second resin members in contact with each other or close to each other such that the laser light is applied to a surface of the second resin member from a side where the first resin member is present, while moving the laser light relative to the first and second resin members; an obtainment apparatus which obtains, as an intensity value, a value corresponding to the intensity of infrared light emitted from the surface of the second resin member, the obtainment apparatus obtaining the intensity value from individual ones of a plurality of locations on the surface as a result of relative movement of the laser light; and a judgment apparatus which judges the state of welding between the first and second resin members, wherein the judgment apparatus judges that the weld state at the surface is good when a value representing the degree of deviation of the intensity value from the average of a predetermined number of successive values, the number being equal to or greater than 2, among the intensity values obtained by the obtainment apparatus falls within a predetermined judgment threshold range.

In a preferred embodiment (12) of the apparatus (11) above, the judgment apparatus successively calculates the average of the predetermined number of values, successively calculates the value representing the degree of deviation, and successively judges whether or not the value representing the degree of deviation falls within the judgment threshold range.

In a fourth aspect (13), the present invention provides an apparatus for manufacturing a welded resin article, comprising: a laser irradiation apparatus which applies laser light to first and second resin members in contact with each other or close to each other such that the laser light is applied to a surface of the second resin member from a side where the first resin member is present, while moving the laser light relative to the first and second resin members; an obtainment apparatus which obtains, as an intensity value, a value corresponding to the intensity of infrared light emitted from the surface of the second resin member, the obtainment apparatus obtaining the intensity value from each individual ones of a plurality of locations on the surface as a result of relative movement of the laser light; and a judgment apparatus which judges the state of welding between the first and second resin members, wherein the judgment apparatus judges that the weld state at the surface is good when at least one of first and second conditions is satisfied, the first condition being that a value calculated as a value relating to the temperature of the surface on the basis of the intensity value obtained by the obtainment apparatus does not fall outside a predetermined temperature threshold range, and the second condition being that a value representing the degree of deviation of the intensity value from the average of a predetermined number of successive values, the number being equal to or greater than 2, among the intensity values obtained by the obtainment apparatus falls within a predetermined judgment threshold range.

BRIEF DESCRIPTION OF THE DRAWINGS

FIG. 19 is a table showing an example of judgment results.

FIG. 21 is a table showing an example of judgment results.

DESCRIPTION OF REFERENCE NUMERALS

Figure 1:
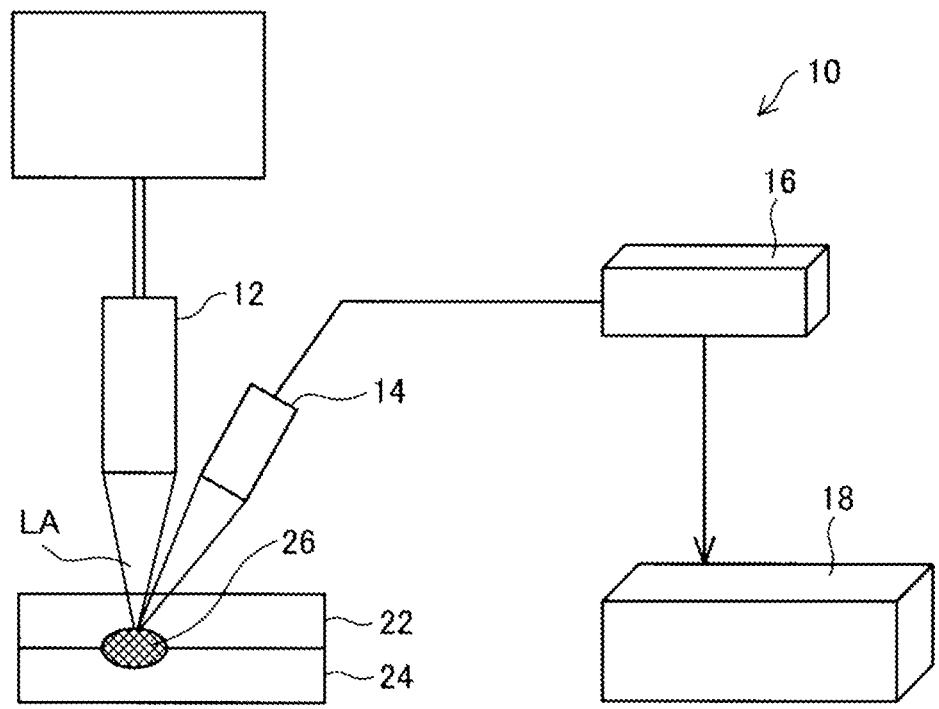
FIG. 1 is an explanatory diagram showing the configuration of a laser welding system used in a manufacturing method of one embodiment of the present invention.

Reference numerals used to identify various features in the drawings include the following.
10: laser welding system
12: laser irradiation apparatus
14: infrared sensor
16: sensor amplifier
18: judgment apparatus
22: laser-light-transmissive resin member
24: laser-light-absorbing resin member
26: weld portion
LA: laser light
WL: welding locus

DETAILED DESCRIPTION OF THE PREFERRED EMBODIMENTS

Next, embodiments of the present invention will be described in the following order and with reference to the drawings. However, the present invention should not be construed as being limited thereto.

A. First Embodiment

A-1. Configuration of a Laser Welding System

FIG. 1 is an explanatory diagram showing the configuration of a laser welding system 10 used in a manufacturing method of one embodiment of the present invention. The laser welding system 10 joins resin members together by laser welding, and judges the weld state.

Figure 2:
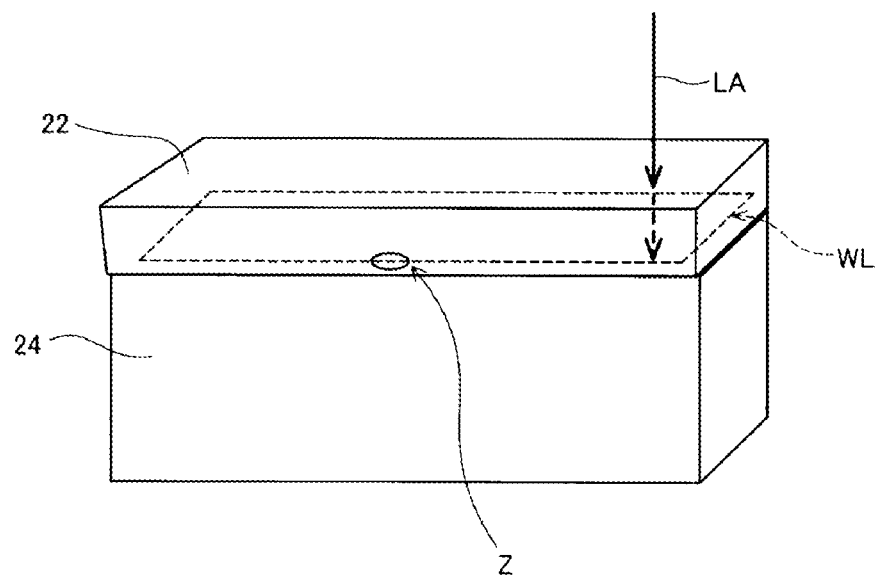
FIG. 2 is an explanatory view of a laser welding process.

The laser welding system 10 includes a laser irradiation apparatus 12 for performing laser welding. FIG. 2 is an explanatory view showing the outline of laser welding. When laser welding is performed, a laser-light-transmissive resin member 22 through which laser light LA can pass and a laser-light-absorbing resin member 24 which absorbs the laser light LA are stacked on each other, and are pressed along the stacking direction by an unillustrated pressing jig. In this state, the laser light LA is applied to the resin members 22 and 24 from the side where the laser-light-transmissive resin member 22 is present, while the laser irradiation apparatus 12 (FIG. 1) is moved relative to the resin members 22 and 24 along a programmed welding path (not shown) which is substantially the same as a welding locus WL. As a result, the laser-light-absorbing resin member 24 is irradiated with the laser light LA passing through the laser-light-transmissive resin member 22, and a portion of the laser-light-absorbing resin member 24 irradiated with the laser light LA generates heat and melts. Also, due to heat transfer from the laser-light-absorbing resin member 24, the surface of the laser-light-transmissive resin member 22 in contact with or located near the laser-light-absorbing resin member 24 also generates heat and melts. The molten portions of the laser-light-transmissive resin member 22 and the laser-light-absorbing resin member 24 form a weld portion 26 (FIG. 1) at and around the boundary between the laser-light-absorbing resin member 24 and the laser-light-transmissive resin member 22, whereby the two members are joined together. Notably, in an example shown in FIG. 2, the welding locus WL is approximately rectangular, and start and end portions of the welding locus WL overlap each other. Also, in the example shown in FIG. 2, a foreign substance Z is present between the laser-light-transmissive resin member 22 and the laser-light-absorbing resin member 24 at a position along the welding locus WL.

A resin which has thermoplasticity and which absorbs the laser light LA without permitting passage of the laser light LA therethrough can be used as the material of the laser-light-absorbing resin member 24. For example, the laser-light-absorbing resin member 24 can be formed of a resin material into which a predetermined colorant such as carbon black, dye, or pigment is mixed. Examples of the resin material include polyamide (PA), polyethylene (PE), polypropylene (PP), polycarbonate (PC), polyoxymethylene (POM), acrylonitrile-butadiene-styrene (ABS), polybutylene terephthalate (PBT), polyphenylene sulfide (PPS), acrylic resin, and polymethyl methacrylate (PMMA).

A resin which has thermoplasticity and which has a predetermined transmissivity for the laser light LA can be used as the material of the laser-light-transmissive resin member 22. For example, the resin material as exemplified above can be used for the laser-light-transmissive resin member 22. In this case, the resin material may contain a colorant so long as the resin material has a predetermined transmissivity for the laser light LA.

A reinforcing fiber such as glass fiber or carbon fiber may be added to the laser-light-transmissive resin member 22 and the laser-light-absorbing resin member 24. Also, the material of the laser-light-transmissive resin member 22 and the material of the laser-light-absorbing resin member 24 are preferably compatible (miscible) with each other.

As the laser light LA, a type of laser light having a certain wavelength is properly selected such that the transmissivity at the laser-light-transmissive resin member 22 which changes depending on the absorption spectrum of the laser-light-transmissive resin member 22 and the thickness (transmission length thereof) becomes equal to or greater than a predetermined value. For example, a YAG laser, a semiconductor laser, a glass-neodymium laser, a ruby laser, a helium-neon laser, a krypton laser, an argon laser, a hydrogen laser, or a nitrogen laser can be used.

The laser welding system 10 (FIG. 1) includes an infrared sensor 14, a sensor amplifier 16, and a judgment apparatus 18. The infrared sensor 14 moves, together with the laser irradiation apparatus 12, relative to the resin members 22 and 24, and detects the temperature at the welding position by obtaining the intensity of infrared light emitted from the welding position during laser welding. Notably, the temperature at the welding position during laser welding means the temperature in a region where the laser-light-transmissive resin member 22 and the laser-light-absorbing resin member 24 are welded together (face each other), the temperature being measured when a predetermined time has elapsed after input of the laser light LA to the laser-light-absorbing resin member 24. Notably, the above-mentioned predetermined time is determined from the positional relation between the laser irradiation apparatus 12 and the infrared sensor 14 and the moving speeds of the laser irradiation apparatus 12 and the infrared sensor 14. The predetermined time is preferably short. A signal representing the intensity of the infrared light detected by the infrared sensor 14 is input to the judgment apparatus 18 after being amplified by the sensor amplifier 16. The judgment apparatus 18 is composed of a computer including a CPU and a memory, and performs weld state judgment processing, described below, through use of the input data relating to the intensity of the infrared light.

A-2. Method of Manufacturing a Welded Resin Article

Figure 3:
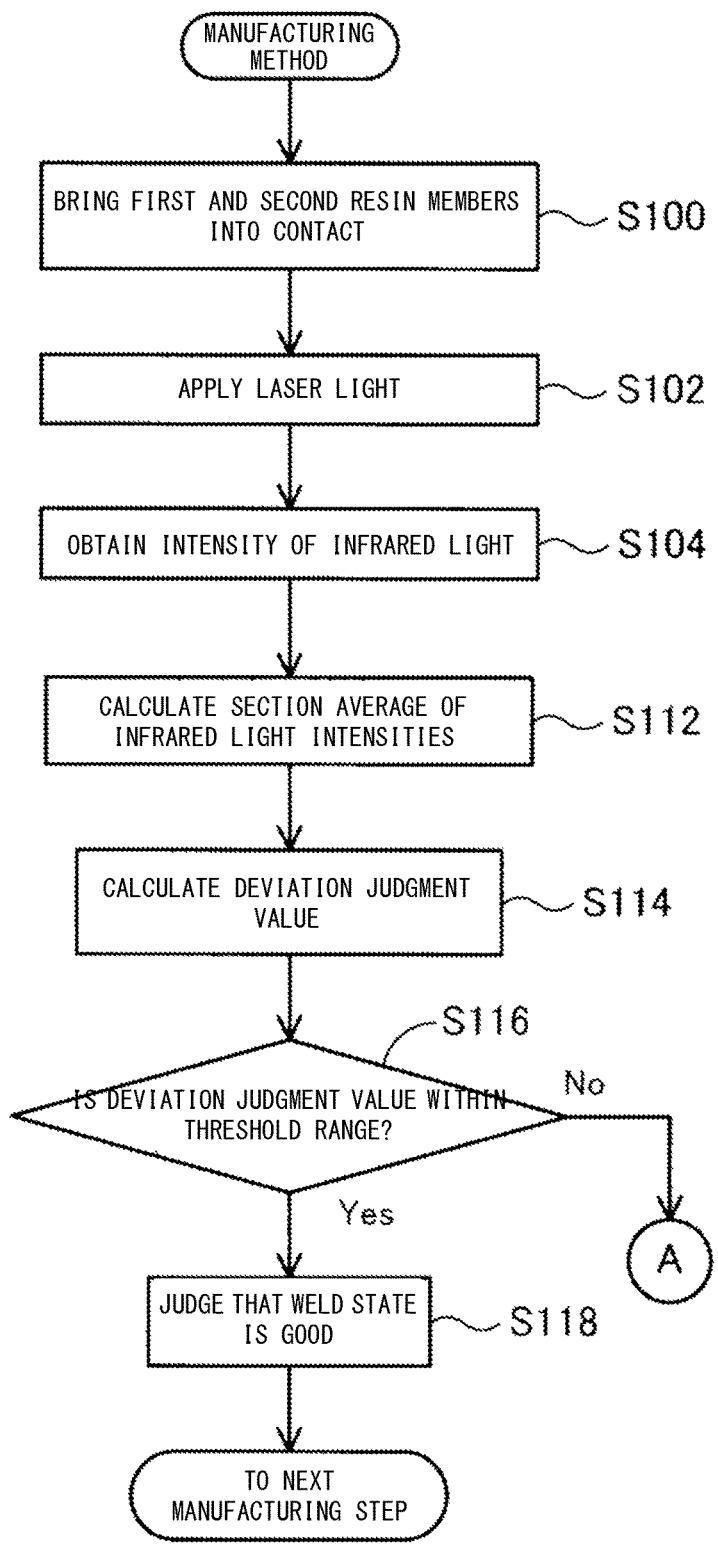
FIG. 3 is a flowchart of a process of manufacturing a welded resin article.
Figure 4:
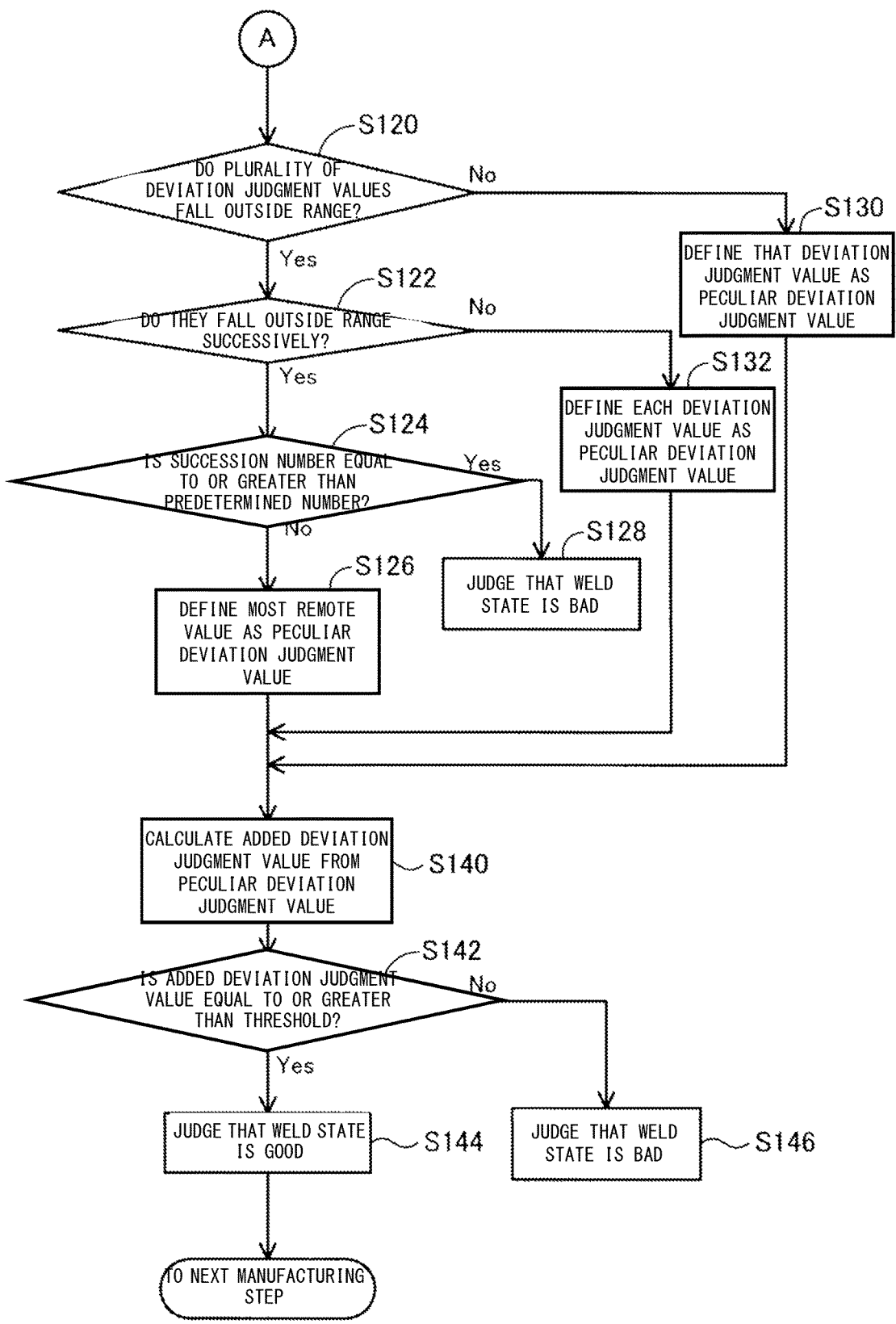
FIG. 4 is a flowchart of the process of manufacturing a welded resin article.

FIGS. 3 and 4 are flowcharts showing a process of manufacturing a welded resin article. In the manufacturing process of the present embodiment, weld state judgment processing is performed so as to judge whether the weld state; i.e., the state of welding between the laser-light-transmissive resin member 22 and the laser-light-absorbing resin member 24 laser-welded together, is good or bad. More specifically, the weld state judgment processing comprises detecting a bad weld state which may be caused by the presence of a foreign substance Z between the laser-light-transmissive resin member 22 and the laser-light-absorbing resin member 24 or on the surface of the laser-light-transmissive resin member 22 at a position along the welding locus WL as in the example shown in FIG. 2.

In the case where the foreign substance Z is present between the laser-light-transmissive resin member 22 and the laser-light-absorbing resin member 24 or on the surface of the laser-light-transmissive resin member 22 at the time of laser welding, the radiated laser light LA is blocked by the foreign substance Z, and does not reach the laser-light-absorbing resin member 24. Therefore, the laser-light-absorbing resin member 24 and the laser-light-transmissive resin member 22 may fail to generate heat and melt sufficiently, which may cause a defective weld state such as a decrease in welding strength and formation of a gap at the welding position. Such a defective weld state is not preferred, because water, gas, or the like may enter a product manufactured by welding through a defective portion thereof and adversely affect the operation of a device (e.g., an electronic circuit) placed therein or corrode a metallic portion, and the welded member may separate from its associated member. The weld state judgment processing is performed so as to judge whether the weld state is good or bad.

In step S100, the laser-light-transmissive resin member 22 and the laser-light-absorbing resin member 24 are brought into contact with each other. In this case, the laser-light-transmissive resin member 22 and the laser-light-absorbing resin member 24 are preferably pressed in the stacking direction, to thereby fix the subject members. Notably, the laser-light-transmissive resin member 22 and the laser-light-absorbing resin member 24 may be arranged so as to be close to each other (i.e., close enough so that the two members are welded to each other when the laser light is passed therethrough) and without contacting each other.

In step S102, the laser irradiation apparatus 12 applies the laser light LA to the surface of the laser-light-absorbing resin member 24 from the side where the laser-light-transmissive resin member 22 is present. Specifically, the laser irradiation apparatus 12 radiates the laser light LA while moving it relative to the laser-light-transmissive resin member 22 and the laser-light-absorbing resin member 24.

In step S104, the infrared sensor 14 obtains a value V corresponding to the intensity of infrared light which is emitted from the surface that is heated due to application of the laser light LA and which has a predetermined wavelength. The infrared sensor 14 obtains the value V from each of a plurality of locations on the surface of the laser-light-absorbing resin member 24 while the laser light LA moves relative to the surface. The wavelength of the infrared light obtained in the present embodiment is 1.5 μm.

In step S112, the judgment apparatus 18 calculates, as a section average, the average of a predetermined number (two or more) of successive values V among the values V corresponding to the intensities of infrared light obtained from the plurality of locations on the surface of the laser-light-absorbing resin member 24.

Figure 5:
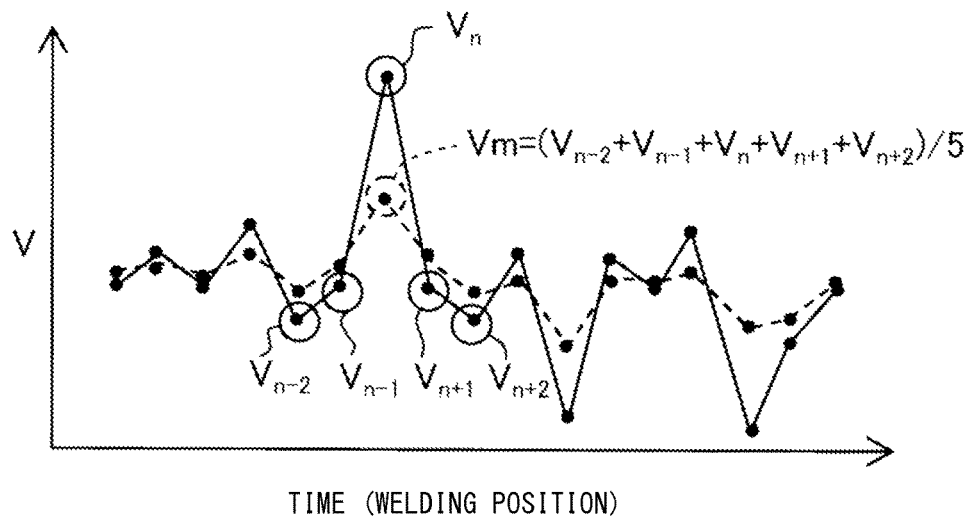
FIG. 5 is an explanatory diagram, in the form of a graph, of an example of the relation between moving average and value corresponding to the intensity of infrared light.

FIG. 5 is an explanatory diagram showing, in the form of a graph, an example of the relation between moving average Vm and value V corresponding to the intensity of infrared light. In the present embodiment, the judgment apparatus 18 calculates, as a section average, the moving average Vm in a section in which a value V corresponding to the intensity of infrared light is contained, on the basis of the value V corresponding to the intensity of infrared light, one or more such values preceding the value V, and one or more such values following the value V. In the example shown in FIG. 5, the judgment apparatus 18 calculates the moving average Vm by averaging five values $V_{n-2}$, $V_{n-1}$, $V_n$, $V_{n+1}$, and $V_{n+2}$.

In step S114 (FIG. 3), the judgment apparatus 18 calculates a deviation judgment value D which represents the degree of deviation, from the section average, of the value V corresponding to the intensity of infrared light. In the case where the degree of deviation from the section average becomes equal to or greater than a predetermined degree at a location, a foreign substance Z is presumed to be present at that location. This is because, when a foreign substance Z is present, the laser light LA is blocked by the foreign substance Z and fails to reach the laser-light-absorbing resin member 24, or the foreign substance Z irradiated with the laser light LA generates heat and burns, whereby a large difference is produced between the value V corresponding to the intensity of infrared light from that location and those corresponding to the intensities of infrared light from other locations.

Figure 6:
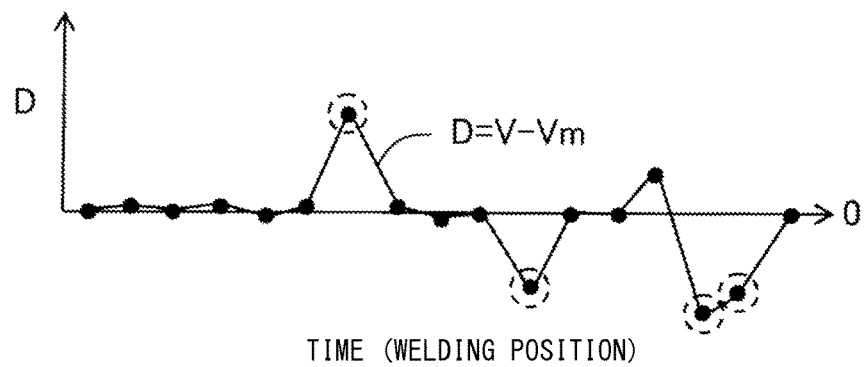
FIG. 6 is an explanatory diagram, in the form of a graph, of example deviation judgment values.

FIG. 6 is an explanatory diagram showing, in the form of a graph, example deviation judgment values D. In the present embodiment, the judgment apparatus 18 calculates a deviation judgment value D by subtracting the corresponding moving average Vm from each value V corresponding to the intensity of infrared light. This makes it possible to properly calculate the degree of deviation, from the section average, of each value V corresponding to the intensity of infrared light. In the example shown in FIG. 6, each deviation judgment value D surrounded by a dotted circle deviates greatly toward the plus side or the minus side.

In step S116 (FIG. 3), the judgment apparatus 18 judges whether or not the deviation judgment value D falls within a predetermined judgment threshold range.

Figure 7:
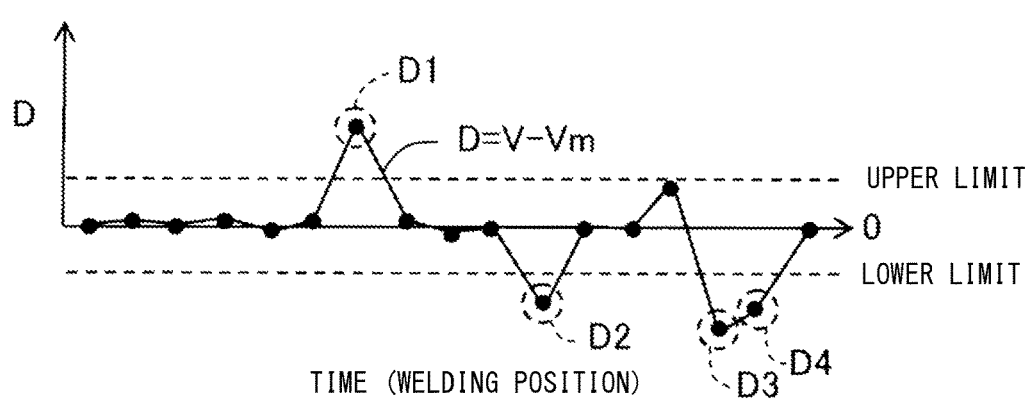
FIG. 7 is an explanatory diagram, in the form of a graph, of an example of an operation of judging whether or not each deviation judgment value falls within a predetermined judgment threshold range.

FIG. 7 is an explanatory diagram showing, in the form of a graph, an example of an operation of judging whether or not each deviation judgment value D falls within the predetermined judgment threshold range. In the example shown in FIG. 7, the predetermined judgment threshold range is set to extend between upper and lower limits, and four deviation judgment values D1, D2, D3, and D4 each surrounded by a dotted circle fall outside the predetermined judgment threshold range. In the case where all the deviation judgment values D fall within the predetermined judgment threshold range (step S116: Yes), the judgment apparatus 18 judges in step S118 that the weld state at the surface of the laser-light-absorbing resin member 24 is good, and moves to the next manufacturing process. This is because, when the deviation judgment values D fall within the predetermined judgment threshold range, no foreign substance Z is presumed to be present, and the weld state at the surface of the laser-light-absorbing resin member 24 is good.

Meanwhile, in the case where the judgment apparatus 18 judges in step S116 that any of the deviation judgment values D falls outside the predetermined judgment threshold range (step S116: No), a foreign substance Z is presumed to be present. Therefore, in step S120 (FIG. 4), the judgment apparatus 18 determines whether or not the deviation judgment values D falling outside the predetermined judgment threshold range are plural in number.

In the case where the deviation judgment values D falling outside the predetermined judgment threshold range are plural in number (step S120: Yes), the judgment apparatus 18 judges in step S122 whether or not the deviation judgment values D falling outside the predetermined judgment threshold range are present successively.

In the example shown in FIG. 7, both of two successive deviation judgment values D3 and D4 each surrounded by a dotted circle fall outside the predetermined judgment threshold range. In the case where the deviation judgment values D falling outside the predetermined judgment threshold range are present successively (step S122: Yes), the judgment apparatus 18 determines in step S124 whether or not the number of the successive deviation judgment values D falling outside the predetermined judgment threshold range (succession number) is equal to or greater than a predetermined number.

In the case where the number of the successive deviation judgment values D falling outside the predetermined judgment threshold range (succession number) is equal to or greater than the predetermined number (step S124: Yes), the judgment apparatus 18 judges in step S128 that the weld state at the surface of the laser-light-absorbing resin member 24 is bad. The reason therefor is as follows.

In the case where the number of the successive deviation judgment values D falling outside the predetermined judgment threshold range is equal to or greater than the predetermined number, the size of the foreign substance Z is presumed to be equal to or greater than a predetermined size. In the case where the size of the foreign substance Z is equal to or greater than the predetermined size, there is a strong possibility that the laser light LA is blocked by the foreign substance Z. Consequently, the last light LA does not reach the laser-light-absorbing resin member 24, and the weld state is not good. Accordingly, in the present embodiment, a judgment as to whether or not the size of the foreign substance Z is equal to or greater than the predetermined size is made, and, when the size of the foreign substance Z is equal to or greater than the predetermined size, the weld state is judged to be bad.

In the present embodiment, in the case where four or more successive deviation judgment values D fall outside the predetermined judgment threshold range, the judgment apparatus 18 judges that the weld state at the surface of the laser-light-absorbing resin member 24 is bad. The reason why the state in which four or more successive deviation judgment values D fall outside the predetermined judgment threshold range is used in the present embodiment as a reference for judging that the weld state is bad is described below.

Figure 8A:
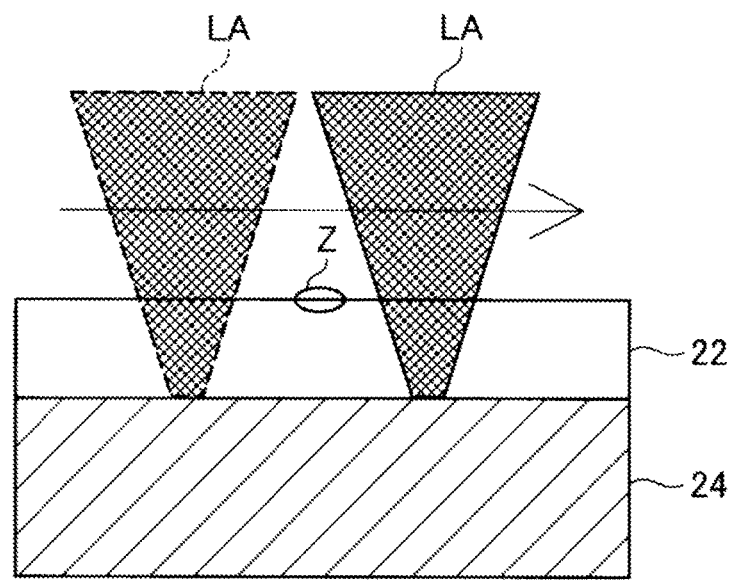
FIGS. 8A and 8B are explanatory views of applying laser light.
Figure 8B:
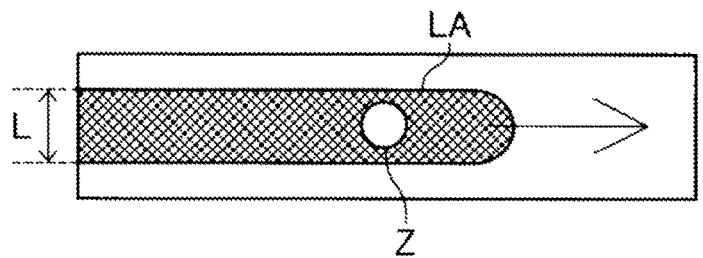

FIGS. 8A and 8B are explanatory views showing application of the laser light LA. FIG. 8A is a cross-sectional view showing the joint interface between the laser-light-transmissive resin member 22 and the laser-light-absorbing resin member 24, and FIG. 8B is an explanatory view of the laser-light-transmissive resin member 22 as viewed from the upper side thereof. In the example shown in FIGS. 8A and 8B, a foreign substance Z adheres to the surface of the laser-light-transmissive resin member 22. When the diameter of the foreign substance Z is less than the spot diameter L of the laser light LA, an unwelded portion is not produced. Meanwhile, when the diameter of the foreign substance Z is greater than the spot diameter L of the laser light LA, an unwelded portion is produced, and the resulting weld state is bad. Accordingly, in the present embodiment, the judgment apparatus 18 judges that the weld state is bad when the diameter of the foreign substance Z is greater than the spot diameter L of the laser light LA.

Figure 9:
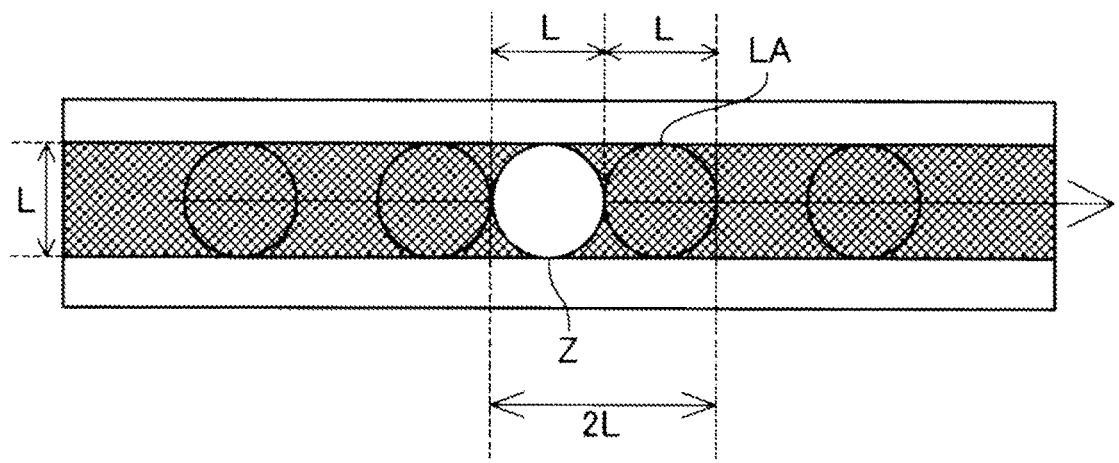
FIG. 9 is an explanatory view of the relation between the spot diameter of laser light and the diameter of a foreign substance.

FIG. 9 is an explanatory view showing the relation between the spot diameter L of the laser light LA and the diameter of the foreign substance Z. In the present embodiment, the following conditions are set for the laser welding system 10.

The spot diameter L of the laser light LA: 1.6 mm
The scanning speed Vz of the laser light LA: 15 mm/s
The data sampling period R: 0.050 s=50 ms In the case where the diameter of the foreign substance Z is equal to the spot diameter L of the laser light LA under the above-described conditions, the laser light LA overlaps with the foreign substance Z while moving over a distance of 2L. The time required for the laser light LA to move over the distance of 2L is 2L/Vz [s]. The number of data sets obtained during that time can be obtained as follows.

$$2L/(Vz \times R) = (2 \times 1.6)/(15 \times 0.050) \approx 4$$

Namely, in the case of the above-mentioned example, when the diameter of the foreign substance Z is equal to the spot diameter L of the laser light LA, four data sets are obtained during a period during which the laser light LA overlaps with the foreign substance Z. In the present embodiment, in the case where four or more successive data sets (deviation judgment values D) fall outside the predetermined judgment threshold range, the judgment apparatus 18 presumes that the diameter of the foreign substance Z is equal to or greater than the diameter L of the laser light LA, and determines that the weld state is bad.

In the case where the judgment apparatus 18 judges in step S124 (FIG. 4) that the number of the successive deviation judgment values D falling outside the predetermined judgment threshold range is not equal to or greater than the predetermined number (step S124: No), in step S126, the judgment apparatus 18 defines, as a peculiar deviation judgment value Dp, a deviation judgment value D which is one of the plurality of successive deviation judgment values D and which is most remote from the predetermined judgment threshold range. In the case where the peculiar deviation judgment value Dp is defined in this manner, of the plurality of the deviation judgment values D, the deviation judgment value D at a position where burning of the foreign substance or blocking of the laser light by the foreign substance becomes most noticeable serves as the peculiar deviation judgment value Dp. As described below, by using the peculiar deviation judgment value Dp as a reference, the judgment apparatus 18 judges whether the foreign substance Z is a combustible foreign substance which burns and vaporizes when it is irradiated with the laser light LA or an incombustible foreign substance which does not burn and remains present even when it is irradiated with the laser light LA.

Figure 10:
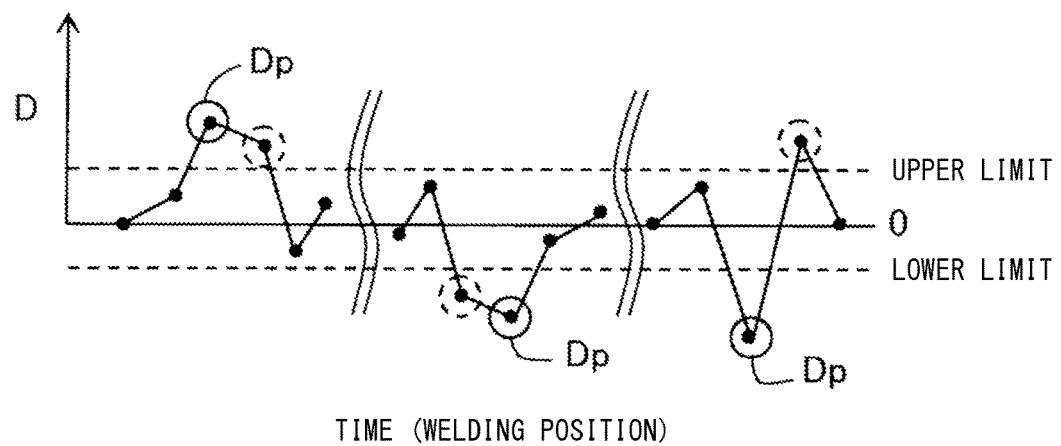
FIG. 10 is an explanatory diagram, in the form of a graph, of an example of the case where a deviation judgment value which is most remote from the predetermined judgment threshold range is defined as a peculiar deviation judgment value.

FIG. 10 is an explanatory diagram showing, in the form of a graph, an example of the case where a deviation judgment value D which is most remote from the predetermined judgment threshold range is defined as the peculiar deviation judgment value Dp. In the example shown in FIG. 10, the deviation judgment values D falling outside the predetermined judgment threshold range are surrounded by dotted circles, and the deviation judgment value D defined as the peculiar deviation judgment value Dp is surrounded by a continuous line circle.

Also, in the case where the judgment apparatus 18 judges in step S120 (FIG. 4) that the deviation judgment values D falling outside the predetermined judgment threshold range are not plural in number (step S120: No), in step S130, the judgment apparatus 18 defines, as the peculiar deviation judgment value Dp, a sole deviation judgment value D falling outside the predetermined judgment threshold range.

Also, in the case where the judgment apparatus 18 judges in step S122 that the deviation judgment values D falling outside the predetermined judgment threshold range are not present successively (step S122: No), in step S132, the judgment apparatus 18 defines each of the deviation judgment values D as the peculiar deviation judgment value Dp.

In step S140, the judgment apparatus 18 calculates an added deviation judgment value Da by adding together the peculiar deviation judgment value Dp, one or more deviation judgment values D preceding the peculiar deviation judgment value Dp, and one or more deviation judgment values D following the peculiar deviation judgment value Dp. In the present embodiment, the judgment apparatus 18 calculates the added deviation judgment value Da by adding together the peculiar deviation judgment value Dp, one deviation judgment value D preceding the peculiar deviation judgment value Dp, and one deviation judgment value D following the peculiar deviation judgment value Dp.

Figure 11:
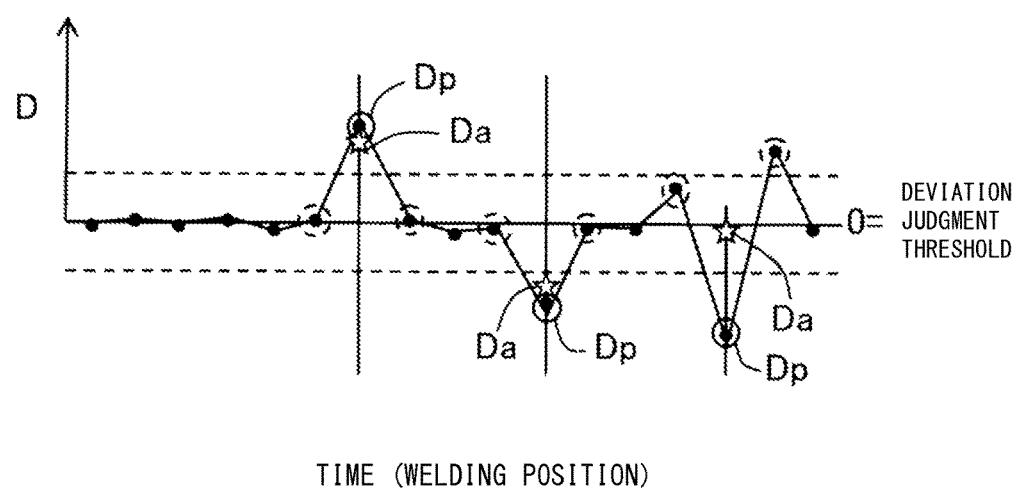
FIG. 11 is an explanatory diagram, in the form of a graph, of the peculiar deviation judgment value, one deviation judgment value preceding the peculiar deviation judgment value, and one judgment value following the peculiar deviation judgment value.

FIG. 11 is an explanatory diagram showing, in the form of a graph, each peculiar deviation judgment value Dp, one deviation judgment value D preceding the peculiar deviation judgment value Dp, and one judgment value D following the peculiar deviation judgment value Dp. In the example shown in FIG. 11, each peculiar deviation judgment value Dp is surrounded by a continuous line circle, and one deviation judgment value D preceding the peculiar deviation judgment value Dp and one judgment value D following the peculiar deviation judgment value Dp are surrounded by dotted circles. FIG. 11 also shows the added deviation judgment value Da.

In step S142 (FIG. 4), the judgment apparatus 18 judges whether the weld state at the surface of the laser-light-absorbing resin member 24 is good or bad by comparing the added deviation judgment value Da and a predetermined deviation judgment threshold. More specifically, the judgment apparatus 18 judges that the weld state is good when the added deviation judgment value Da is equal to or greater than the predetermined deviation judgment threshold, and judges that the weld state is bad when the added deviation judgment value Da is less than the predetermined deviation judgment threshold. In the present embodiment, the deviation judgment threshold is set to 0. The reason why such a judgment is made is as follows.

In the case where the foreign substance Z is a combustible foreign substance which vaporizes when irradiated with the laser light LA, the foreign substance Z instantaneously generates heat and ignites upon irradiation with the laser light LA. Therefore, each of the peculiar deviation judgment value Dp and the deviation judgment values D preceding and following the peculiar deviation judgment value Dp becomes a large value equal to or greater than 0. As a result, in the case where the foreign substance Z is a combustible foreign substance, the added deviation judgment value Da becomes equal to or greater than the predetermined deviation judgment threshold. Since a combustible foreign substance Z vaporizes upon irradiation with laser light, the resulting weld state at the surface is good.

In contrast, in the case where the foreign substance Z is an incombustible foreign substance which does not vaporize even when it is irradiated with the laser light LA, the laser light LA is blocked by the foreign substance Z and does not reach the surface of the laser-light-absorbing resin member 24. Therefore, each of the peculiar deviation judgment value Dp and the deviation judgment values D preceding and following the peculiar deviation judgment value Dp becomes smaller than 0. As a result, in the case where the foreign substance Z is an incombustible foreign substance, the added deviation judgment value Da becomes less than the predetermined deviation judgment threshold. Therefore, according to the present embodiment, by comparing the added deviation judgment value Da with the predetermined deviation judgment threshold, it is possible to judge whether the foreign substance is a combustible foreign substance or an incombustible foreign substance, to thereby properly determine whether the weld state is good or bad.

As described above, in the present embodiment, since the presence/absence of a foreign substance can be detected, a welded resin article whose weld state is good can be manufactured. Moreover, in the present embodiment, even in the case where a foreign substance is present, when the foreign substance is combustible, the weld state is judged to be good. Therefore, it is possible to reduce the possibility that the weld state is erroneously judged to be bad despite actually being good.

B. Second Embodiment

Figure 12:
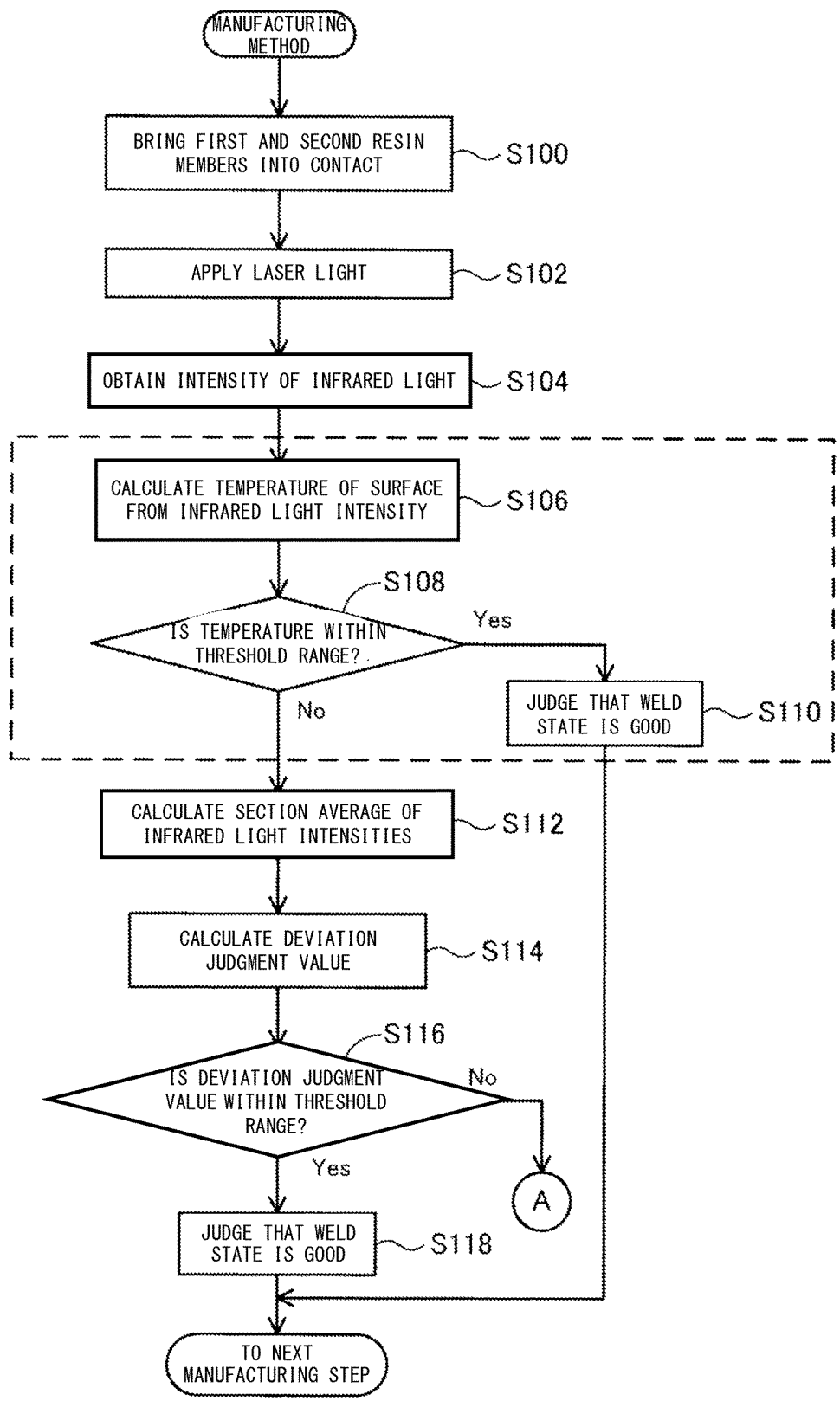
FIG. 12 is a flowchart a process of manufacturing a welded resin article in a second embodiment.

FIG. 12 is a flowchart showing the flow of a process of manufacturing a welded resin article in a second embodiment. The flowchart shown in FIG. 12 corresponds to the flowchart of the first embodiment shown in FIG. 3. The second embodiment differs from the first embodiment shown in FIG. 3 in that steps S106 to S110 (steps surrounded by a dotted frame) are added, and the other steps are the same as those of the first embodiment.

In step S106, the judgment apparatus 18 calculates a value T relating to the temperature at the surface of the laser-light-absorbing resin member 24 irradiated with the laser light LA, on the basis of the value V corresponding to the intensity of infrared light.

In step S108, the judgment apparatus 18 judges whether or not the value T relating to the temperature (hereinafter also referred to as the "temperature related value T") deviates from a predetermined temperature threshold range. The reason why this judgment is made is as follows. In the case where a foreign substance is present on the surface of the laser-light-transmissive resin member 22 or between the laser-light-transmissive resin member 22 and the laser-light-absorbing resin member 24, the value T relating to the temperature at the surface of the laser-light-absorbing resin member 24 irradiated with the laser light LA deviates from the predetermined temperature threshold range.

In the case where the temperature related value T falls within the predetermined temperature threshold range (step S108: Yes), the judgment apparatus 18 judges in step S110 that the weld state at the surface of the laser-light-absorbing resin member 24 is good, and moves to the next manufacturing process.

Meanwhile, in the case where the temperature related value T falls outside the predetermined temperature threshold range (step S108: No) (i.e., the judgment apparatus 18 does not judge in step S112 that the weld state at the surface of the laser-light-absorbing resin member 24 is good), the judgment apparatus 18 calculates, as a section average, the average of a predetermined number (two or more) of successive values V among the values V corresponding to the intensities of infrared light obtained from the plurality of locations on the surface of the laser-light-absorbing resin member 24. The steps subsequent thereto are the same as those of the first embodiment.

As described above, according to the second embodiment, the presence/absence of a foreign substance can be detected based on the temperature related value T. Therefore, it is possible to judge that the weld state is good when a foreign substance is absent, and to manufacture a welded resin article having a good weld state.

C. Third Embodiment

Figure 13:
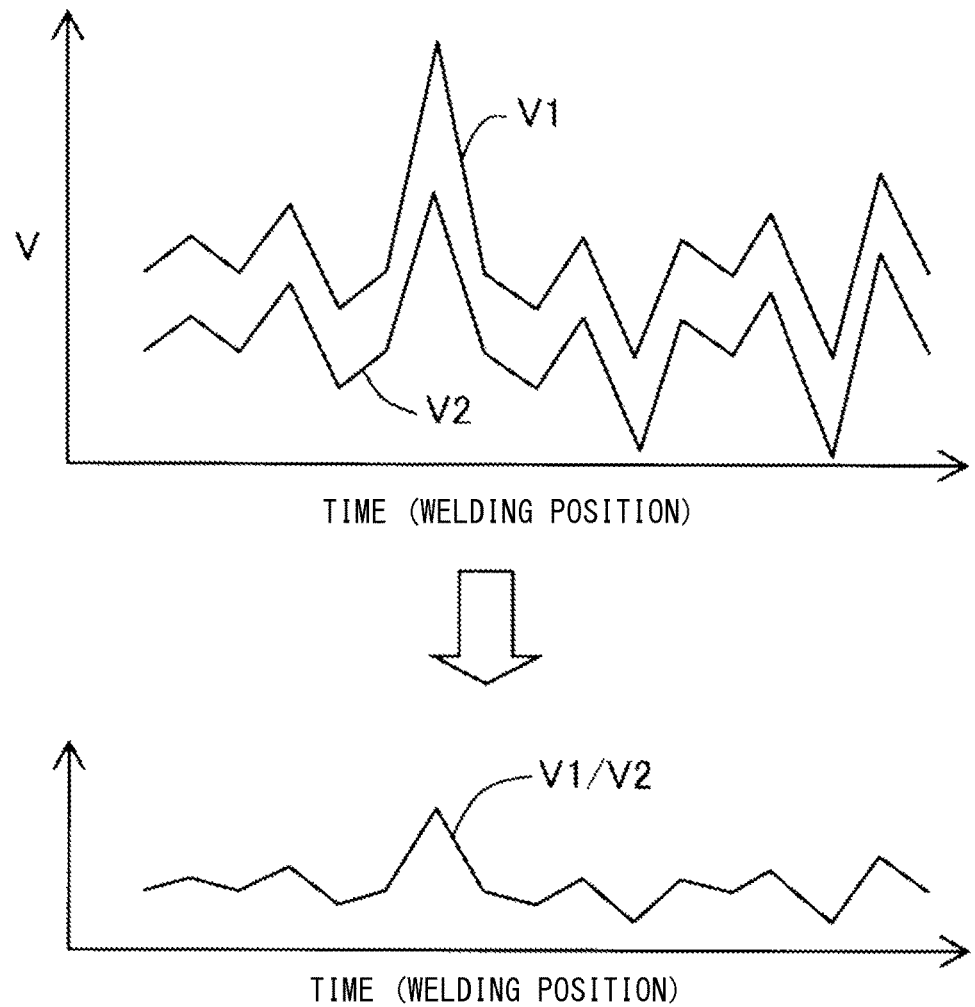
FIG. 13 is an explanatory diagram, in the form of a graph, of values corresponding to the intensities of two infrared lights having different wavelengths, which values are obtained in a third embodiment.

FIG. 13 is an explanatory diagram showing, in the form of a graph, values V1 and V2 corresponding to the intensity of two infrared lights having different wavelengths, which values are obtained in a third embodiment. In the third embodiment, in step S104 (FIGS. 3 and 12) in the first and second embodiments, the judgment apparatus 18 obtains the values V1 and V2 corresponding to the intensities of two infrared lights having different wavelengths, and calculates the value of V1/V2 which is the ratio between the obtained two values V1 and V2 corresponding to the intensities of the two infrared lights. In step S106 and steps subsequent thereto, the judgment apparatus 18 uses the calculated value of V1/V2 as the value V corresponding to the intensity of infrared light. Even when the judgment apparatus 18 is configured as described above, as in the case of the first and second embodiments, the judgment apparatus 18 can judge whether the weld state at the surface of the laser-light-absorbing resin member 24 is good or bad. Also, in the case where the value relating to the temperature at the surface of the laser-light-absorbing resin member 24 is calculated, a two-color method can be used. Therefore, the temperature related value T can be calculated accurately. For example, the temperature related value T can be calculated in accordance with the following expression.

$$T = T1/T2/A \text{ ($A$ is a scaling factor, and, for example, } A=0.004)$$

D. Fourth Embodiment

In a fourth embodiment, in step S104 (FIGS. 3 and 12) in the first and second embodiments, the judgment apparatus 18 obtains values corresponding to the intensities of two or more infrared lights having different wavelengths, and performs the steps subsequent to step S104 for each of the values corresponding to the intensities of the two or more infrared lights. In the case where the judgment that the weld state is bad is made for at least one value corresponding to the intensity of infrared light having a certain wavelength, the judgment apparatus 18 judges that the weld state is bad. Therefore, the fourth embodiment can yield the same effects as those of the first and second embodiments, and can improve the accuracy in judging the weld state because the weld state is judged based on the values corresponding to the intensities of two or more infrared lights.

E. Fifth Embodiment

In a fifth embodiment, in step S112 (FIGS. 3 and 12) of the first through fourth embodiments, the judgment apparatus 18 calculates a designated-section average Vs instead of the moving average Vm. The designated-section average Vs is the average of the values corresponding to the intensities of infrared light in each of predetermined sections. For example, the judgment apparatus 18 designates first through fifth data sets (values corresponding to the intensity of infrared light) as data in a single section, and calculates the average of the first through fifth data sets as the designated-section average Vs. Subsequently, the judgment apparatus 18 designates sixth through tenth data sets as data in a single section, and calculates the average of the sixth through tenth data sets as the designated-section average Vs. Even when the judgment apparatus 18 is configured as described above, as in the case of the first through fourth embodiments, it is possible to properly judge whether the weld state at the surface of the laser-light-absorbing resin member 24 is good or bad.

F. Examples of Weld State Judgment

F-1. First Example of Judgment Results

Figure 14:
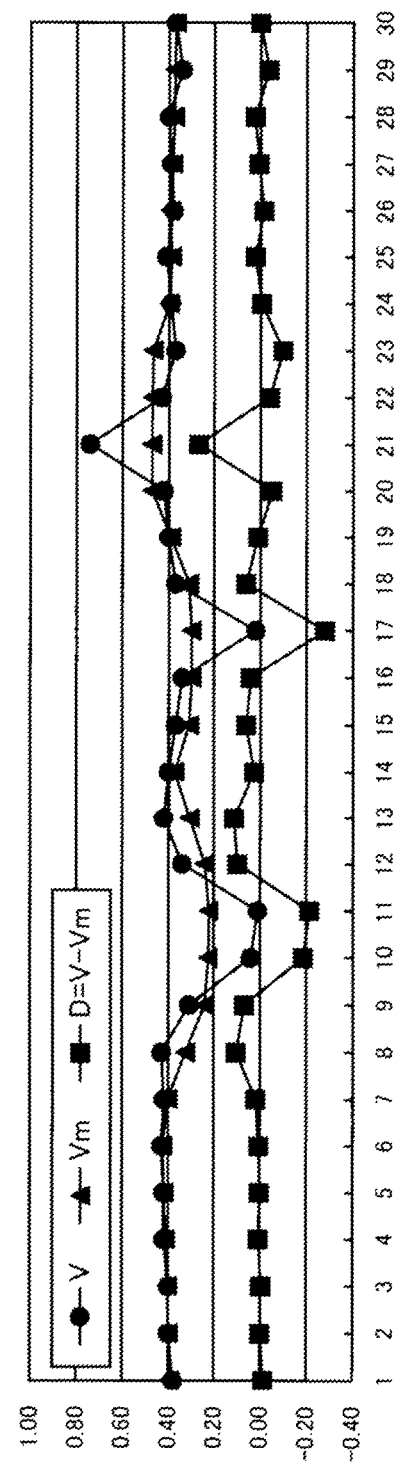
FIG. 14 is a table and graph showing an example of judgment results.

FIG. 14 includes a table and a graph showing an example of judgment results. In the example shown in FIG. 14, the judgment was made under the following conditions.
Basic manufacturing method: the first embodiment
Section average: a moving average Vm was used. The moving average Vm was calculated from a value V at the center, two values V which precede the value V at the center, and two values V which follow the value V at the center.
Method of calculating the deviation judgment value D:
D=V−Vm
When the deviation judgment value D fell within the range of −0.15 to +0.15, the weld state was judged to be good.
When the added deviation judgment value Da was equal to or greater than 0, it was judged that the foreign substance was combustible and the weld state was good.

Notably, at welding positions Nos. 1, 2, 29, and 30, data of the two values V which precede the value V at the center and the two values V which follow the value V at the center could not be obtained. Therefore, the moving average Vm at welding position No. 1 was calculated from data of the values V at welding positions Nos. 1, 2, and 3; the moving average Vm at welding position No. 2 was calculated from data of the values V at welding positions Nos. 1, 2, 3, and 4; the moving average Vm at welding position No. 29 was calculated from data of the values V at welding positions Nos. 27, 28, 29, and 30; and the moving average Vm at welding position No. 30 was calculated from data of the values V at welding position Nos. 28, 29, and 30.

Also, in the table of FIG. 14, the case where the weld state was determined to be good is indicated as "OK," and the case where the weld state was determined to be bad is indicated as "NG." This also applies to the tables of FIGS. 15, 16, 17, 18, 19, and 21.

In the example shown in FIG. 14, on the basis of the deviation judgment values D, foreign substances were judged to be present at position Nos. 10, 11, 17, and 21. The deviation judgment values D at positions No. 11, No. 17, No. 21 were employed as peculiar deviation judgment values Dp. On the basis of the added deviation judgment value Da, it was judged that a foreign substance at position No. 21 is combustible and the weld state at that position is good, and foreign substances positions No. 11 and No. 17 are incombustible, and the weld states at these positions are bad. As a result, it was judged that the weld states at position No. 11 and No. 17 are bad.

F-2. Second Example of Judgment Results

Figure 15:
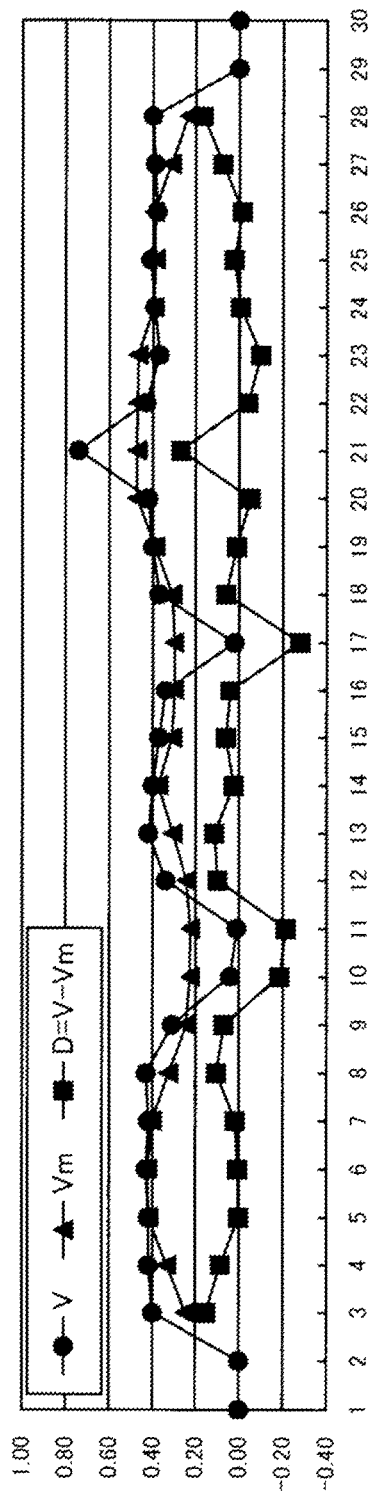
FIG. 15 is a table and graph showing an example of judgment results.

FIG. 15 includes a table and a graph showing an example of judgment results. The example shown in FIG. 15 differs from the example shown in FIG. 14 in the following points.
Application of laser light is started at position No. 3 and is ended at position No. 28.
In the case where the moving average Vm is calculated from values at welding positions including any of welding positions Nos. 1, 2, 29, and 30 at which the laser light is not applied, the judgment based on the deviation judgment value D is not performed.
According to the example shown in FIG. 15, it is possible to reduce the possibility that an erroneous judgment is made in the vicinity of the welding start position and in the vicinity of the welding end position.

F-3. Third Example of Judgment Results

Figure 16:
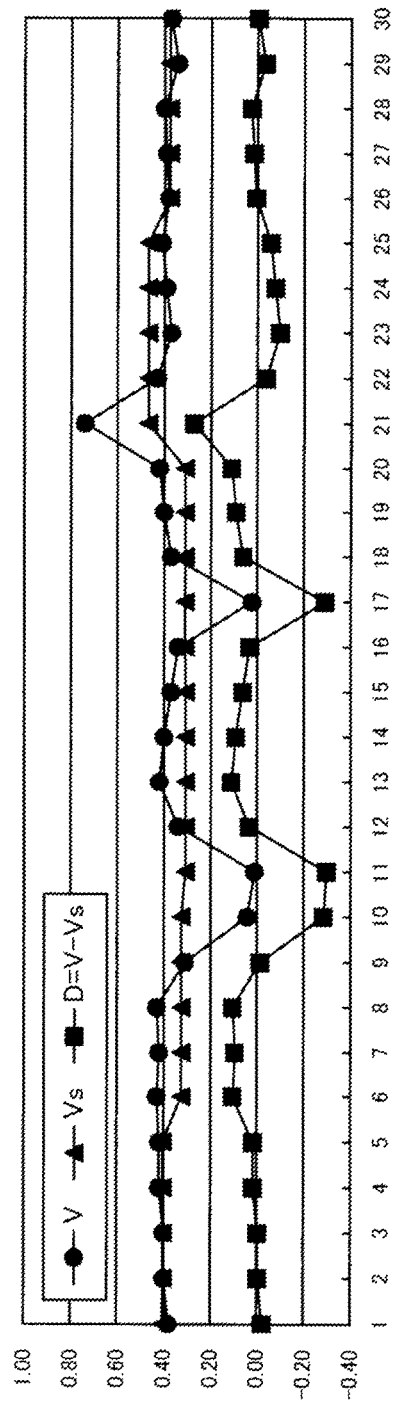
FIG. 16 is a table and graph showing an example of judgment results.

FIG. 16 includes a table and a graph showing an example of judgment results. In the example shown in FIG. 16, the judgment was made under the following conditions.
Basic manufacturing method: the first embodiment+the fifth embodiment Section average: the designated-section average Vs was used. The designated-section average Vs was calculated from five data sets which were regarded as data in a single section.

Method of calculating the deviation judgment value D: D=V−Vs

When the deviation judgment value D fell within the range of −0.15 to +0.15, the weld state was judged to be good.

When the added deviation judgment value Da was equal to or greater than 0, it was judged that the foreign substance was combustible and the weld state was good.

Since the judgment results in the example shown in FIG. 16 are the same as those of the example shown in FIG. 14, their description is omitted. Even in the case where the judgment was made under the above-mentioned conditions, it is possible to properly judge whether the weld state at the surface of the laser-light-absorbing resin member 24 is good or bad.

F-4 Fourth Example of Judgment Results

Figure 17:
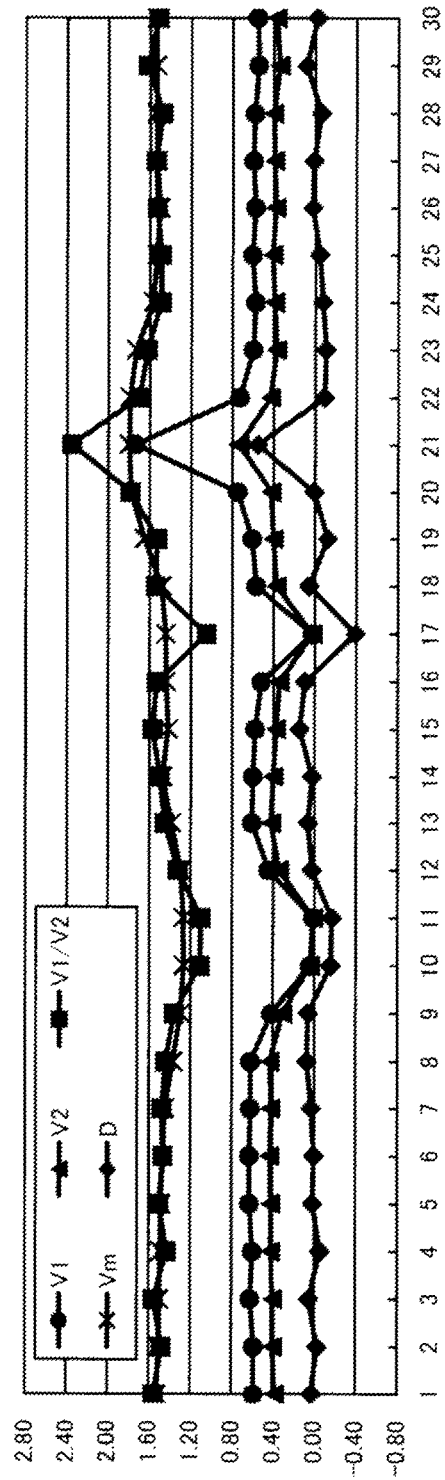
FIG. 17 is a table and graph showing an example of judgment results.

FIG. 17 includes a table and a graph showing an example of judgment results. In the example shown in FIG. 17, the judgment was made under the following conditions.

Basic manufacturing method: the first embodiment+the third embodiment

Section average: the moving average Vm was used. The moving average Vm was calculated from a value V at the center, two values V which precede the value V at the center, and two values V which follow the value V at the center.

Method of calculating the deviation judgment value D: D=V1/V2−Vm

When the deviation judgment value D fell within the range of −0.15 to +0.15, the weld state was judged to be good.

When the added deviation judgment value Da is equal to or greater than 0, it was judged that the foreign substance was combustible and the weld state was good.

Since the judgment results in the example shown in FIG. 17 are the same as those of the example shown in FIG. 14, their description is omitted. Even in the case where the judgment was made under the above-mentioned conditions, it is possible to properly judge whether the weld state at the surface of the laser-light-absorbing resin member 24 is good or bad.

F-5. Fifth Example of Judgment Results

Figure 18:
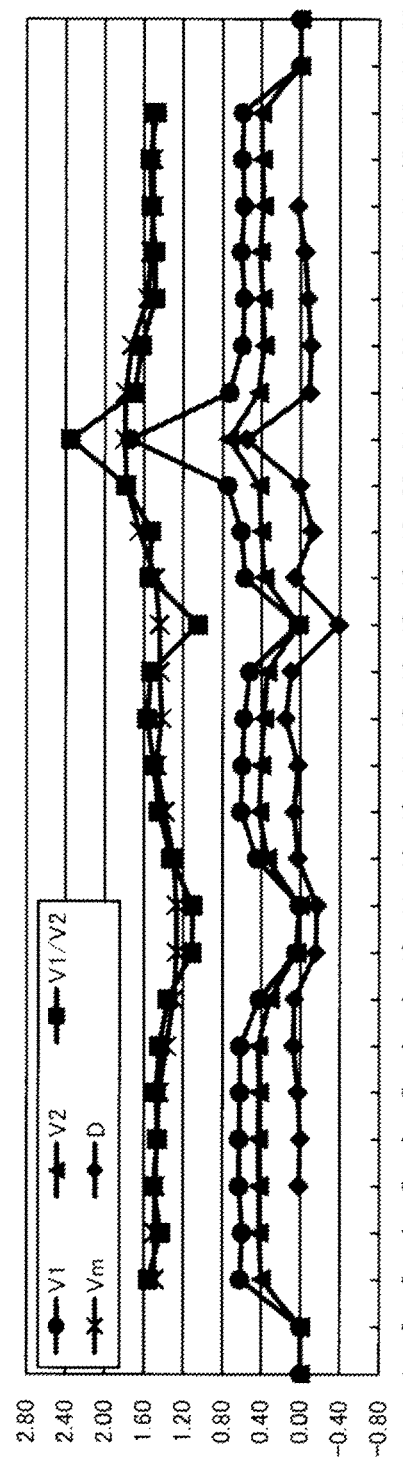
FIG. 18 is a table and graph showing an example of judgment results.

FIG. 18 includes a table and a graph showing an example of judgment results. The example shown in FIG. 18 differs from the example shown in FIG. 17 in the following points.

Application of laser light is started at position No. 3 and is ended at position No. 28.

In the case where the moving average Vm is calculated from values at welding positions including any of welding positions Nos. 1, 2, 29, and 30 at which the laser light is not applied, the judgment based on the deviation judgment value D is not performed.

According to the example shown in FIG. 18, it is possible to reduce the possibility that an erroneous judgment is made in the vicinity of the welding start position and in the vicinity of the welding end position.

F-6 Sixth Example of Judgment Results

Figure 19:
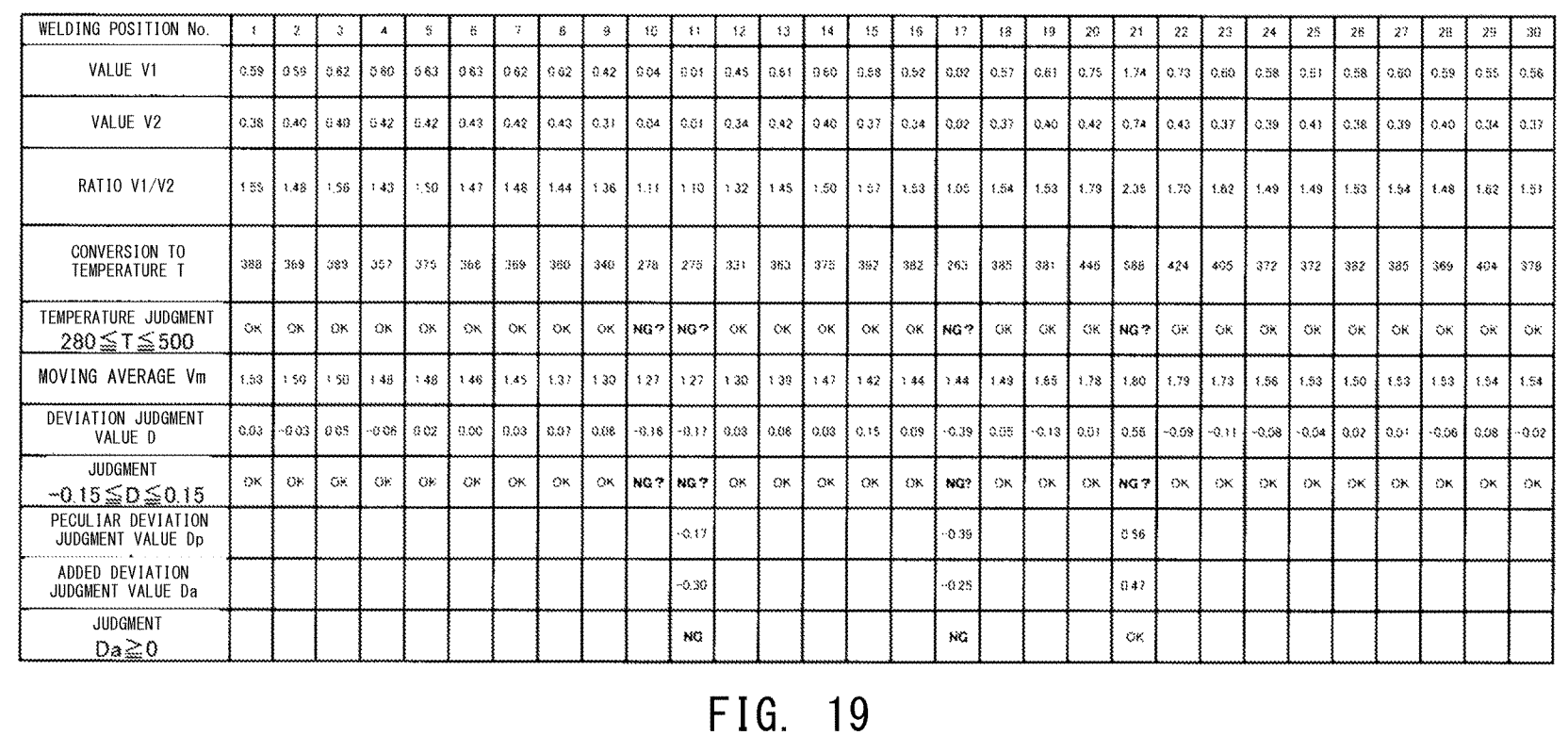
Figure 20:
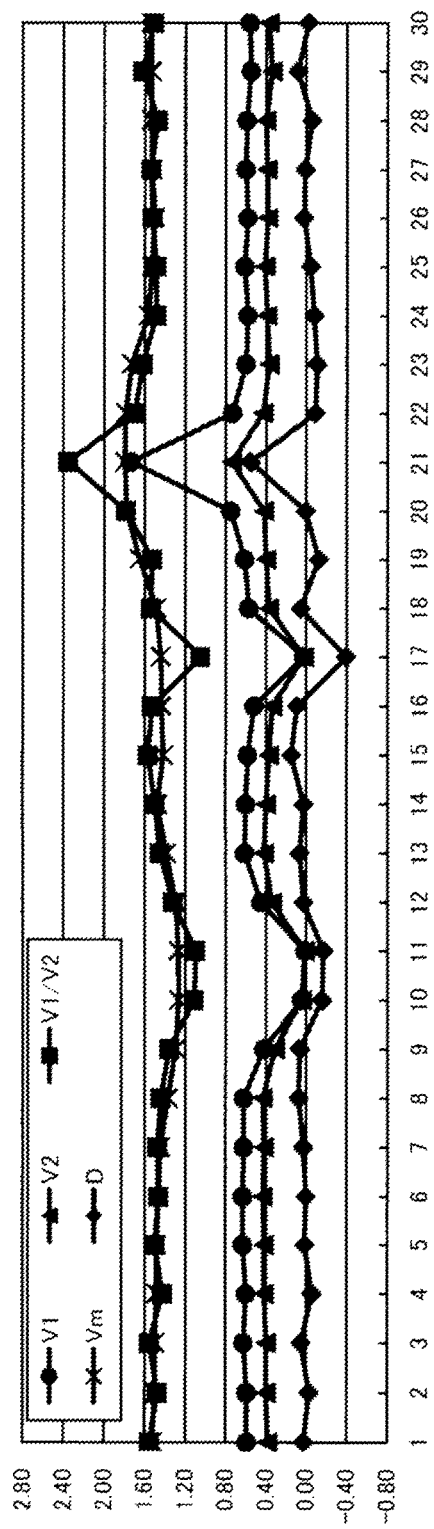
FIG. 20 are graphs showing the judgment results of FIG. 19.
Figure 20:
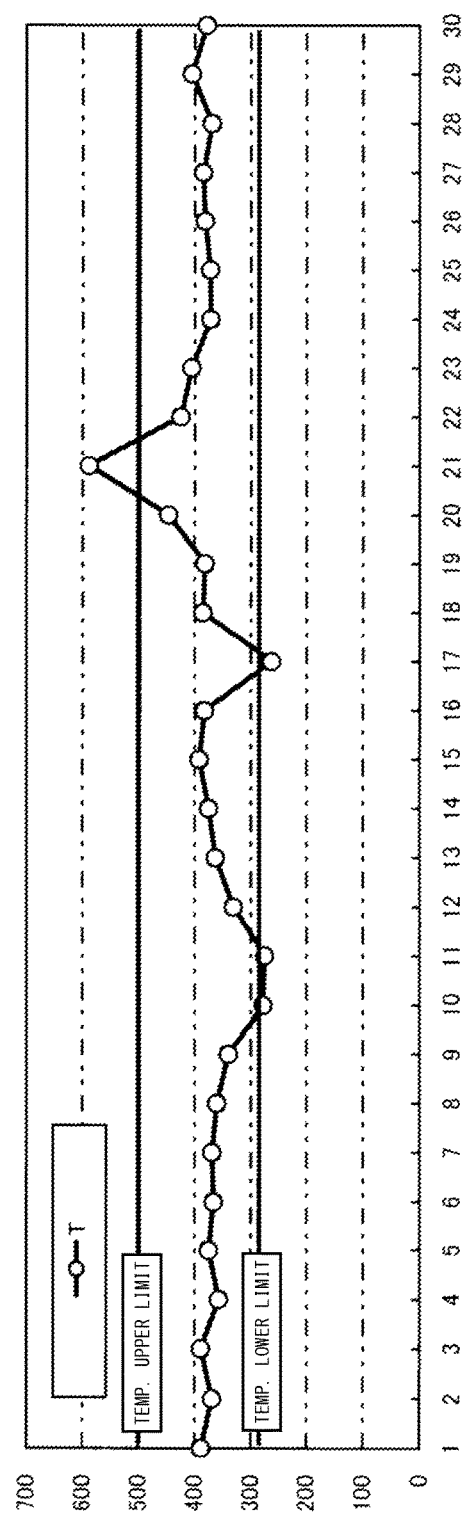

FIG. 19 is a table showing an example of judgment results. FIG. 20 is a graph showing the judgment results of FIG. 19. In the example shown in FIGS. 19 and 20, the judgment was made under the following conditions.

Basic manufacturing method: the first embodiment+the second embodiment+the third embodiment Conversion to temperature T: T=V1/V2/0.004

When the temperature T fell within the range of 280 to 500, it was judged that the weld state was good.

Section average: the moving average Vm was used. The moving average Vm was calculated from a value V at the center, two values V which precede the value V at the center, and two values V which follow the value V at the center.

Method of calculating the deviation judgment value D: D=V1/V2−Vm

When the deviation judgment value D fell within the range of −0.15 to +0.15, the weld state was judged to be good.

When the added deviation judgment value Da was equal to or greater than 0, it was judged that the foreign substance was combustible and the weld state was good.

In the example shown in FIG. 19, on the basis of the temperature T, the weld state was judged to be good at welding positions other than welding position Nos. 10, 11, 17, and 21. Since other judgment results are the same as those in the example shown in FIG. 14, their description is omitted. Even in the case where the judgment is made under the above-mentioned conditions, it is possible to properly judge whether the weld state at the surface of the laser-light-absorbing resin member 24 is good or bad. Notably, at the welding positions where the weld state is judged to be good by the judgment based on the temperature T, the judgment based on the deviation judgment value D or the added deviation judgment value Da may be omitted.

F-7. Seventh Example of Judgment Results

Figure 21:
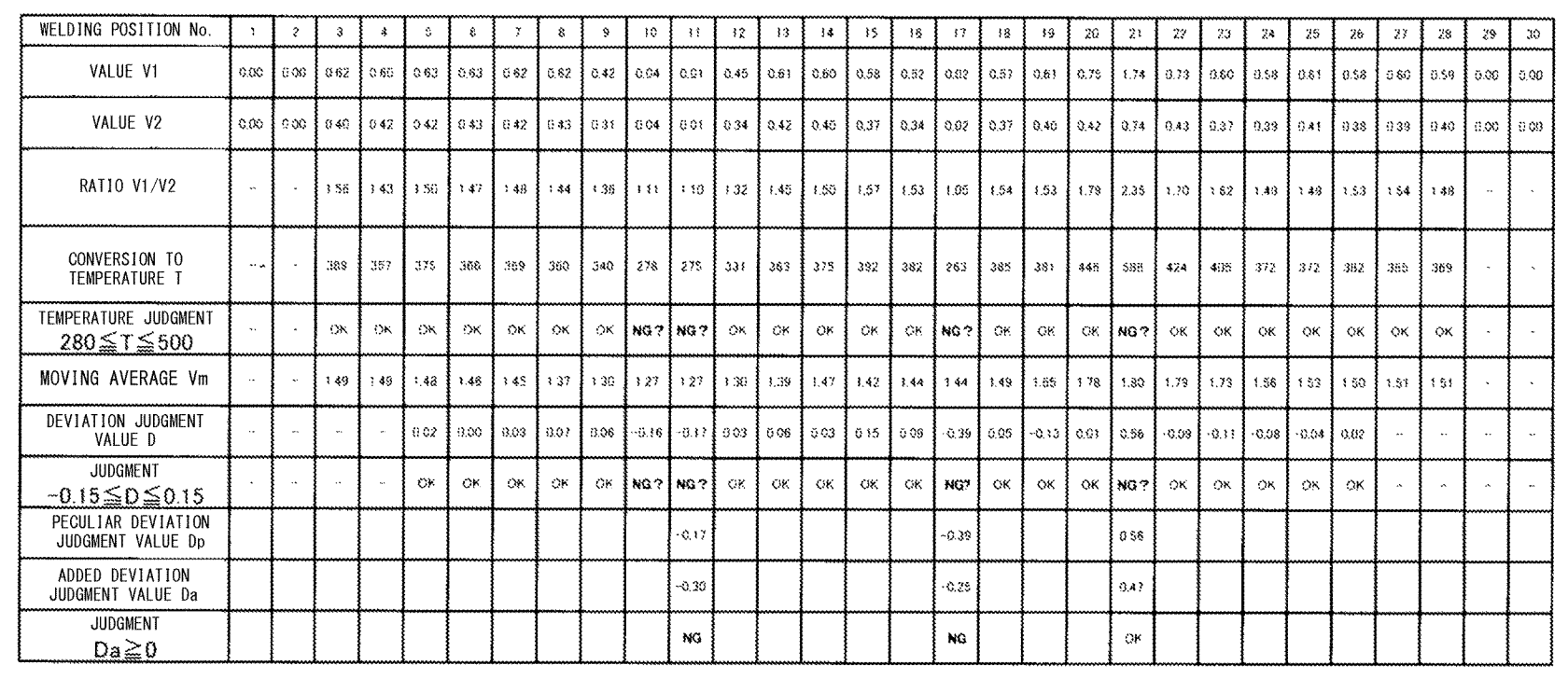
Figure 22:
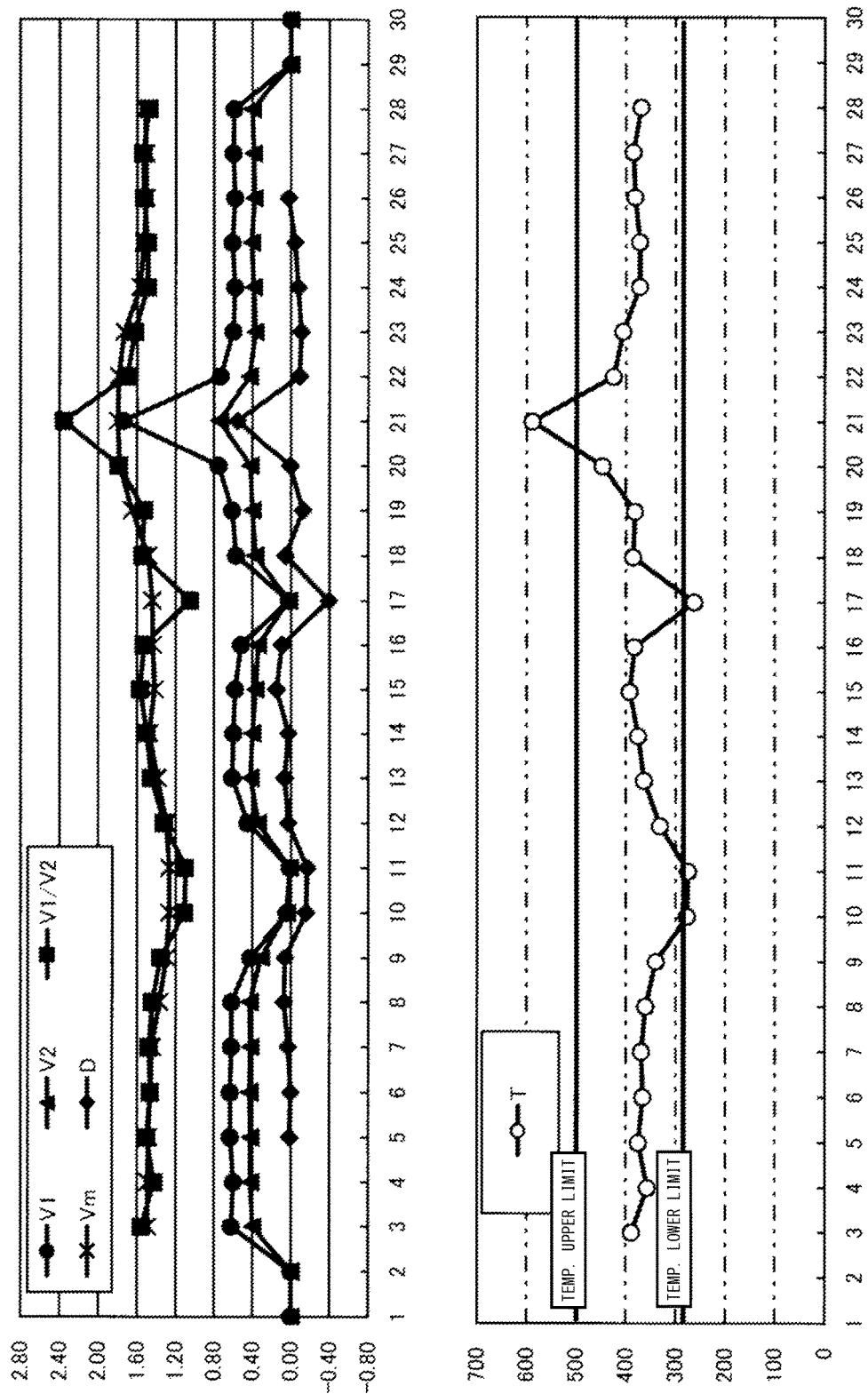
FIG. 22 are graphs showing the judgment results of FIG. 21.

FIG. 21 is a table showing an example of judgment results. FIG. 22 includes graphs showing the judgment results of FIG. 21. The example shown in FIGS. 21 and 22 differs from the example shown in FIGS. 19 and 20 in the following points.

Application of laser light is started at position No. 3 and is ended at position No. 28.

In the case where the moving average Vm is calculated from values at welding positions including any of welding position Nos. 1, 2, 29, and 30 at which the laser light is not applied, the judgment based on the deviation judgment value D is not performed.

According to the example shown in FIGS. 21 and 22, it is possible to reduce the possibility that an erroneous judgment is made in the vicinity of the welding start position and in the vicinity of the welding end position.

G. Modifications

Notably, the present invention is not limited to the above-described embodiment, and may be carried out in various forms without departing from the scope of the invention. For example, the following modifications are possible.

First Modification:

In the above-described embodiments, the judgment apparatus 18 calculates the deviation judgment value D by subtracting the section average from the value V corresponding to the intensity of infrared light. In contrast, in this modification, the judgment apparatus 18 may calculate the deviation judgment value D by dividing the value V corresponding to the intensity of infrared light by the section average. Alternatively, the judgment apparatus 18 may calculate the deviation judgment value D by a statistical method other than averaging. For example, the judgment apparatus 18 may calculate the deviation judgment value D which represents the degree of deviation by obtaining a weighted average, a median, a mode, a standard deviation or the like through use of other statistical methods.

Second Modification:

In the above-described embodiments, various resin products may be manufactured by joining resin members. For example, a resin housing may be manufactured. In the above-described embodiments, a member having a laser-light-absorbing resin applied to the surface thereof may be used instead of the laser-light-absorbing resin member 24. The laser light radiated from the laser irradiation apparatus 12 may be pulsed laser light.

Third Modification:

In the above-described embodiments, the steps after step S104 may be performed after the intensities of infrared light at all the positions are obtained in step S104, or may be performed after the intensities of infrared light at the positions in a certain section are obtained. Alternatively, while the laser light is applied, the steps after step S104 may be performed for only the intensities of infrared light obtained upon application of the laser light. Also, the manufacturing process may be ended when the weld state is judged to be bad.

Fourth Modification:

A portion of the functions realized by software in the above-described embodiments may be realized by hardware, and a portion of the functions realized by hardware in the above-described embodiments may be realized by software.

Fifth Modification:

Each of the above-described embodiments may be understood as a method of manufacturing a welded resin article by laser-welding together a first resin member which allows laser light to pass therethrough and a second resin member which absorbs the laser light, the method comprising the steps of applying laser light to a surface of the second resin member from a side where the first resin member is present, judging whether or not a foreign substance is present on the basis of an intensity of light emitted from the surface irradiated with the laser light; judging, when no foreign substance is present, that the weld state is good and judging, when a foreign substance is present, whether the foreign substance is combustible or incombustible on the basis of the intensity of the light; and judging, when the foreign substance is judged to be combustible, that the weld state is good.

Sixth Modification:

An apparatus which brings the laser-light-transmissive resin member 22 and the laser-light-absorbing resin member 24 in contact with each other or close to each other in step S100 may or may not be contained in the laser welding system 10. Such an apparatus may be realized, for example, by a robot arm.

The present invention is not limited to the above-described embodiments, examples, and modifications, and can be realized in various configurations without departing from the scope of the invention. For example, the technical features in the embodiments, examples, and modifications which correspond to the technical features in the modes described in the "Summary of the Invention" section may be freely combined or replaced with other technical features so as to solve some or all of the above-mentioned problems or to achieve some or all of the above-mentioned effects. Also, those technical features which are not described in the present specification as essential technical features may be freely omitted.

This application is based on Japanese Patent Application No. JP 2013-189300 filed Sep. 12, 2013 and Japanese Patent Application No. JP 2014-088648 filed Apr. 23, 2014, incorporated herein by reference in their entirety.

What is claimed is:

1. A method of manufacturing a welded resin article by laser-welding together a first resin member which allows laser light to pass therethrough and a second resin member which absorbs the laser light, the method comprising:
    (a) bringing the first resin member and the second resin member into contact with each other or close to each other;
    (b) applying the laser light to a surface of the second resin member from a side where the first resin member is present, while moving the laser light relative to the first and second resin members;
    (c1) obtaining a value corresponding to the intensity of infrared light emitted from the surface that is heated as a result of applying the laser light, the value being obtained from individual ones of a plurality of locations on the surface as a result of relative movement of the laser light;
    (d) successively calculating a section average which is the average of a predetermined number of successive values, the number being equal to or greater than 2, among the values obtained from the plurality of locations on the surface and each corresponding to the intensity of the infrared light;
    (e) successively calculating a deviation judgment value representing the degree of deviation of the value corresponding to the intensity of the infrared light from the section average; and
    (f) successively judging whether or not the deviation judgment value falls within a predetermined judgment threshold range and judging that a weld state at the surface is good when the deviation judgment value falls within the judgment threshold range,
    wherein the step (f) includes:
    defining as a peculiar deviation judgment value a deviation judgment value which does not fall within the predetermined judgment threshold range and calculating an added deviation judgment value by adding together the peculiar deviation judgment value, one or more deviation judgment values preceding the peculiar deviation judgment value and one or more deviation judgment values following the peculiar deviation judgment value; and
    judging whether the weld state at the surface is good or bad by comparing the added deviation judgment value with a predetermined deviation judgment threshold.

2. The method of manufacturing a welded resin article as claimed in claim 1, wherein the step (c1) includes obtaining values corresponding to the intensities of two infrared lights having different wavelengths, and the method includes calculating a ratio between the values corresponding to the intensities of the two infrared lights and using the ratio as the value corresponding to the intensity of the infrared light.

3. The method of manufacturing a welded resin article as claimed in claim 1, wherein the step (c1) includes obtaining values corresponding to the intensities of two or more infrared lights having different wavelengths, and the steps subsequent to the step (c1) are performed for each of the values corresponding to the intensities of the two or more infrared lights having different wavelengths.

4. The method of manufacturing a welded resin article as claimed in claim 1, wherein the section average in the step (d) is a moving average in a section in which the value corresponding to the intensity of the infrared light is contained, the moving average being calculated from the value corresponding to the intensity of the infrared light, one or more such values preceding the value corresponding to the intensity of the infrared light, and one or more such values following the value corresponding to the intensity of the infrared light.

5. The method of manufacturing a welded resin article as claimed in claim 1, wherein the step (e) comprises calculating the deviation judgment value by subtracting the section average from the value corresponding to the intensity of the infrared light.

6. A method of manufacturing a welded resin article as claimed in claim 1, wherein the step (f) includes a step which is performed when a plurality of deviation judgment values falling outside the predetermined judgment threshold range are present successively and which comprises defining, as the peculiar deviation judgment value, one of the plurality of successive deviation judgment values which is most remote from the predetermined judgment threshold range.

7. The method of manufacturing a welded resin article as claimed in claim 1, wherein the step (f) includes judging that the weld state at the surface is bad when a predetermined number of deviation judgment values falling outside the predetermined judgment threshold range are present successively.

8. The method of manufacturing a welded resin article as claimed in claim 1, wherein the welded resin article is a resin housing.

9. A method of manufacturing a welded resin article by laser-welding together a first resin member which allows laser light to pass therethrough and a second resin member which absorbs the laser light, the method comprising:
  (a) bringing the first resin member and the second resin member into contact with each other or close to each other;
  (b) applying the laser light to a surface of the second resin member from a side where the first resin member is present, while moving the laser light relative to the first and second resin members;
  (c1) obtaining a value corresponding to the intensity of infrared light emitted from the surface that is heated as a result of applying the laser light, the value being obtained from individual ones of a plurality of locations on the surface as a result of relative movement of the laser light;
  (c2) calculating a value relating to the temperature of the surface irradiated with the laser light based on the value corresponding to the intensity of the infrared light;
  (c3) judging whether or not the value relating to the temperature falls outside a predetermined temperature threshold range and judging that a weld state at the surface is good when the value relating to the temperature does not fall outside the predetermined temperature threshold range;
  (d) calculating, when the weld state at the surface is not judged in the step (c3) to be good, a section average which is the average of a predetermined number of successive values, the number being equal to or greater than 2, among the values obtained from the plurality of locations on the surface and each corresponding to the intensity of the infrared light;
  (e) calculating a deviation judgment value representing the degree of deviation of the value corresponding to the intensity of the infrared light from the section average; and
  (f) judging whether or not the deviation judgment value falls within a predetermined judgment threshold range and judging that the weld state at the surface is good when the deviation judgment value falls within the predetermined judgment threshold range,
  wherein the step (f) includes:
  defining as a peculiar deviation judgment value a deviation judgment value which does not fall within the predetermined judgment threshold range and calculating an added deviation judgment value by adding together the peculiar deviation judgment value, one or more deviation judgment values preceding the peculiar deviation judgment value and one or more deviation judgment values following the peculiar deviation judgment value; and
  judging whether the weld state at the surface is good or bad by comparing the added deviation judgment value with a predetermined deviation judgment threshold.

10. The method of manufacturing a welded resin article as claimed in claim 9, wherein the step (c1) includes obtaining values corresponding to the intensities of two infrared lights having different wavelengths, and the method includes calculating a ratio between the values corresponding to the intensities of the two infrared lights and using the ratio as the value corresponding to the intensity of the infrared light.

11. The method of manufacturing a welded resin article as claimed in claim 9, wherein the step (c1) includes obtaining values corresponding to the intensities of two or more infrared lights having different wavelengths, and the steps subsequent to the step (c1) are performed for each of the values corresponding to the intensities of the two or more infrared lights having different wavelengths.

12. The method of manufacturing a welded resin article as claimed in claim 9, wherein the section average in the step (d) is a moving average in a section in which the value corresponding to the intensity of the infrared light is contained, the moving average being calculated from the value corresponding to the intensity of the infrared light, one or more such values preceding the value corresponding to the intensity of the infrared light, and one or more such values following the value corresponding to the intensity of the infrared light.

13. The method of manufacturing a welded resin article as claimed in claim 9, wherein the step (e) comprises calculating the deviation judgment value by subtracting the section average from the value corresponding to the intensity of the infrared light.

14. A method of manufacturing a welded resin article as claimed in claim 9, wherein the step (f) includes a step which is performed when a plurality of deviation judgment values falling outside the predetermined judgment threshold range are present successively and which comprises defining, as the peculiar deviation judgment value, one of the plurality of successive deviation judgment values which is most remote from the predetermined judgment threshold range.

15. The method of manufacturing a welded resin article as claimed in claim 9, wherein the step (f) includes judging that the weld state at the surface is bad when a predetermined number of deviation judgment values falling outside the predetermined judgment threshold range are present successively.

16. The method of manufacturing a welded resin article as claimed in claim 9, wherein the welded resin article is a resin housing.

\* \* \* \* \*